United States Patent [19]
Hartmann et al.

[11] Patent Number: 5,854,227
[45] Date of Patent: Dec. 29, 1998

[54] THERAPEUTIC DERIVATIVES OF DIPHOSPHONATES

[76] Inventors: John F. Hartmann, 1 Woodmeadow La., Princeton Junction, N.J. 08550; Dan Farcasiu, 4729 Bayard St., Pittsburgh, Pa. 15213

[21] Appl. No.: 473,787

[22] Filed: Jun. 7, 1995

Related U.S. Application Data

[63] Continuation-in-part of Ser. No. 206,113, Mar. 4, 1994, abandoned.

[51] Int. Cl.$^6$ ................. A61K 31/43; A61K 31/545; A61K 31/495; C07F 9/02
[52] U.S. Cl. .............. 514/79; 540/215; 540/217; 540/300; 540/301; 540/302; 540/304; 540/308; 540/200; 546/23; 546/24; 568/8; 568/10
[58] Field of Search ................. 540/222, 221, 540/215, 217, 300–302, 304, 308, 200; 514/79, 80, 81, 82–101; 544/105, 361; 546/23, 24; 568/8, 10

[56] References Cited

U.S. PATENT DOCUMENTS

| | | | |
|---|---|---|---|
| 4,621,077 | 11/1986 | Rosini et al. | 514/108 |
| 4,746,654 | 5/1988 | Breliere et al. | 514/108 |
| 4,820,698 | 4/1989 | Degenhardt | 514/102 |
| 4,922,007 | 5/1990 | Kieczykowski et al. | 562/13 |
| 4,939,284 | 7/1990 | Degenhardt | 558/142 |
| 5,220,021 | 6/1993 | Dunn et al. | 544/140 |
| 5,270,365 | 12/1993 | Gertz et al. | 514/108 |
| 5,284,841 | 2/1994 | Chu et al. | 514/183 |
| 5,374,721 | 12/1994 | Schoen et al. | 540/491 |
| 5,524,544 | 6/1996 | O'Meara et al. | 102/287 |

OTHER PUBLICATIONS

The Merck Index, Ninth Edition, (Jan. 1976) pp. 919, 1174.

*Primary Examiner*—Matthew V. Grumbling
*Attorney, Agent, or Firm*—Donald J. Perrella

[57] ABSTRACT

Novel chemotherapeutic agents having utility in treating infectious diseases such as periodontal disease, certain urinary tract infections, infectious urinary tract stones, and bone cancer, are obtained by combining chemically a diphosphonate compound with a therapeutic agent effective against the foregoing diseases.

20 Claims, No Drawings

THERAPEUTIC DERIVATIVES OF DIPHOSPHONATES

RELATED APPLICATION

The present application is a continuation-in-part of our application Ser. No. 08/206,113 filed 04 Mar. 1994 now abandoned.

BACKGROUND OF THE INVENTION

Osteomyelitis is a painful and debilitating condition caused by a variety of micro-organisms, mainly *Staphylococcus aureus*. This disease occurs more commonly in children. Within the adult population, diabetics and kidney dialysis patients also are vulnerable. The acute form of the disease is treatable with antibiotics, but requires a lengthy period of daily therapy. It can, however, revert to a recurrent or chronic form requiring repeated hospital stays and treatment regimens. The remarks of Waldvogel et al. in their 1980 review continue to be relevant today:

"The high success rate observed with antibiotic therapy in most bacterial diseases contrasts with the substantial failure rate in the treatment of bone infections." (1980) *New Eng. J. Med.* 303:360.

Urinary catheters are the most common source of nosocomial infections. The bacteriuria which may result from the catheterization is serious because it is a predisposing factor to Gram-negative septicemia, a disease with a high rate of mortality. Kunin stated the consequences of this infectious nidus succinctly:

"Systemic antimicrobial therapy is ineffective in eradicating catheter-associated infections other than temporarily." (1987) *Detection, Prevention and Management of Urinary Tract Infections*, Chapt. 5, pp. 247–297.

Urinary calculi can develop anywhere in the urinary tract. They are hard, mineralized substances producing pain, obstructions and secondary infections. Basically there are two types of urinary stones: metabolic, originating through metabolic dysfunctions, and infectious, associated with bacterial infections. Infection persists in 40% of patients treated with antibiotics, and a full 60% of those develop recurring stones. Left untreated, infected calculi can result in kidney loss and even death in 25% of such cases. Some metabolic stones become contaminated and bacteria are entrapped within the interstices during its crystallization. Such infected stones are notoriously resistant to eradication. Current treatment of infectious urinary calculi involves surgical removal with concomitant administration of antimicrobial agents.

Broadly speaking, there are two categories of periodontal disease: gingivitis and periodontitis, both generated by micro-organisms in dental plaque on the tooth surface. Both conditions are characterized by an inflammation of the gingiva, the gum tissue at the base of the teeth. Periodontitis also involves bone erosion and loss of dentition over a long period of time. Burt (1992) *Clin. Geriat. Med.* 3:447.

Osteosarcoma is an exceedingly malignant tumor that usually occurs in children and young adults. The type and extent of the tumor determines the type of treatment which ranges from variously-administered chemotherapeutic agents to limb amputation in conjunction with chemotherapy.

U.S. Pat. No. 4,621,077 discloses diphosphonic acids of general formula

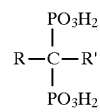

wherein R is fluorine or a linear or branched optionally substituted alkyl radical containing between 1 and 5 carbon atoms and R' is OH or fluorine. These compounds are useful in treating urolithiasis or as inhibitors of bone reabsorption.

U.S. Pat. No. 4,746,654 discloses methylene diphosphonic acid derivatives useful as anti-inflammatory agents.

U.S. Pat. No. 4,922,007 discloses an improved process for the preparation of 4-amino-1-hydroxybutane-1,1-disphosphonic acid.

U.S. Pat. No. 5,220,021 discloses geminal diphosphonate derivatives of an unsaturated 5-membered diheterocycloaliphatic ring useful as anti-arthritic agents.

French published patent application 2 683 527 discloses cortisone derivatives of gem-bisphonates.

French published patent application 2 683 528 discloses nonsteroidal antiinflammatory arylacetic and aryl proponic acid derivatives of gem-bisphonics.

French published patent application 2 683 529 discloses gem-diphosphonate analogs of cis-platinum.

U.S. Pat. No. 5,524,544 discloses methylene diphosphonic acid derivatives useful as inhibitors of cholesterol biosynthesis.

Japanese published patent application 90-104593 discloses compounds of the formula $ACO[R(CH_2)_nCO]_m NHCH(PO_3H_2)_2$ wherein ACO is the residue of diclofenac or flufenamic acid, R=NH or O, m=0 or 1 and n=1–10.

OBJECTS OF THE INVENTION

It is an object of the present invention to provide pharmaceutically active agents having utility for treating various diseases, especially bone diseases. Further objects are to provide new, pharmaceutically active chemical entities for treating osteomyelitis, urinary catheter-related infections, infectious urinary calculi, periodontal disease and osteosarcoma, and to provide methods for employing these new pharmaceutically active chemical entities in treatment of disease. Another object is to provide novel intermediates for preparing these new chemical entities. Still another object is to provide methods for the preparation of the foregoing materials. These and other objects of the present invention will be apparent from the following description.

SUMMARY OF THE INVENTION

Novel chemotherapeutic agents having utility in treating infectious diseases such as osteomyelitis, periodontal disease, certain urinary tract infections, infectious urinary tract stones, and bone cancer are obtained by combining chemically a diphosphonate (also called bisphosphonate) compound with a pharmaceutically active chemical entity effective against the foregoing diseases.

DETAILED DESCRIPTION

The novel pharmaceutically active therapeutic chemical agents of the present invention are diphosphonate (also called bisphosphonate) derivatives of therapeutic agents effective in treating infectious diseases such as osteomyelitis, periodontal disease, certain urinary tract infections, infectious urinary tract stones, and bone cancer. The diphosphonate groups cause the therapeutic agent to be attracted to, and to concentrate on, the surfaces of various salt crystals and the more complex forms of such crystals, such as hydroxyapatite, a major constituent of bone and the surface of dentition. Bacteria associated with these crystals are thereby exposed to an elevated concentration of the therapeutic agent, relative to the surrounding milieu. Organisms harbored in bone (osteomyelitis), at the gum-dentition interface (periodontal disease), on the surface of salt-encrusted indwelling urinary catheters and in infectious urinary calculi, are targeted by the therapeutic agents.

Because of the relative inaccessibility of micro-organisms in this protected environment, there is a dangerous tendency on the part of attending physicians to treat these infections through indiscriminate use of antibiotics. This often leads to the development of resistant forms, a frequent occurrence, for example, in urinary tract infections. When treated according to the present invention, however, not only are the free-floating, planktonic organisms neutralized by the therapeutic agents disclosed herein but, more importantly, the source of the infection, namely the sessile forms adhering to the catheter are attacked.

Chemotherapy of osteosarcoma is another area in which the therapeutic agents of the present invention provide a two-part therapeutic advantage over agents not containing diphosphonate groups. Diphosphonate derivatives of antineoplastic drugs like methotrexate and adriamycin concentrate in bone tissue, thereby allowing lower effective doses to be employed, thus attenuating their toxicity and reducing side effects.

Diphosphonic acid compounds useful as intermediates in the present invention have the general formula V'—R—Z (1) wherein V' is halogen, preferably Cl, Br and I, OH, SH, NR'R", COOR', CO—X wherein X is halogen or azido, O—CO—X wherein X is halogen, O—CO—OR', CO—SR', S—CO—X, NR'—CO—X, NR'—NHR", NR'—CN, NR'—C(=NH)—NH—CN, or metal (covalently bound or ionic), for example, Li, Na or Mg, wherein R, R' and R" are independently hydrogen or an organic group and Z is

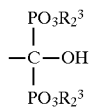

wherein each $R^3$ is independently H, alkyl or substituted alky of from 1 to about 10 carbons that may be linear or branched, saturated or unsaturated; cycloalkyl or substituted cycloalkyl of from 3 to about 10 carbons that may be saturated or unsaturated; monocyclic or polycyclic aryl such as, for example phenyl or naphthyl, optionally substitued by halogen, trifluoromethyl, alkyl of 1 to about 4 carbons, nitro, amino, hydroxy or carboxyl; aralkyl or substituted aralkyl, that is to say alkyl carrying an aryl substituent wherein the alkyl group has from 1 to about 10 carbons that may be linear or branched, saturated or unsaturated; or a saturated 5- or 6-membered heterocyclic such as, for example, piperidine, morpholine and piperazine, or 5- or 6-membered unsaturated heterocyclic such as, for example pyridine, furan, thiophene, pyrazine, pyrimidine, purine and imidazole. If desired or necessary, the OH group of Z may be protected by techniques established and known in the art.

Pharmaceutically active chemical entities useful in the present invention have the general formula A—V' wherein A is the residue of a pharmaceutically active chemical entity and V' has the meaning given above.

The compounds of the present invention have the general formula and A—(V)$_m$—(R)$_n$—Z (2) wherein m and n are independently 0 or 1, A, R, and Z have the meanings given above and V is one of, but not limited to, O, S, NR', CONR', CO—O, O—CO, O—CO—O, CO—S, S—CO, S—CO—S, NR'—CO, O—CO—NR', NR'—CO—O, NR'—CO—NR", CO—NR'—NR", NR'—NR"—CO, NR'—C(=NH)—NR", NR'—C(=NH)—NH—C(=NH)—NR" or another acyclic or cyclic aliphatic or heteroorganic connecting structural unit; R, R', R", and Z are as defined above, and R" is hydrogen or an organic group that can be the same as R' or can be different from R'. Compounds of the foregoing formula wherein either n or m is 1, or wherein both n and m are 1 are obtained by reacting various compounds of formula (1) with a pharmaceutically active chemical entity of formula A—V' carrying a functional group or substituent appropriate for the formation of the connecting structural unit by the chemical reaction.

Thus, when the pharmaceutically active chemical entity contains a halogen atom, it can be reacted with a diphosphonate compound of formula V'—R—Z (1) wherein V' is primary or secondary amino to eliminate hydrogen halide and yield a compound of the formula A—NR'—R—Z (3), which corresponds to formula (2) with n and m=1, and V=NR' wherein R' is H or an organic group; it can also be reacted with a reactant containing two primary or secondary amino groups in an acyclic or cyclic structure and with a compound of formula (1) or (1a) wherein Y is halogen, to give a compound of formula (2) wherein n=1 and V is a connecting group attached by nitrogen atoms (—NR'—) to both A and R. Compounds of formula (3) can, however, be obtained as well by reacting a pharmaceutically active chemically entity compound containing a primary or secondary amino group with a compound of formula (1) containing a halogen atom.

Alternatively, when the pharmaceutically active chemical entity contains a carboxylic group, or a reactive carboxyl group derivative (e.g, acyl halide ester or azide), it can be reacted with a compound of formula (1) wherein V' is a primary or secondary amino group to eliminate water or another molecule as results from the corresponding condensation reaction and form a compound of the formula A—CO—NR'—R—Z (13), which corresponds to (2) with m=1, and n=1 and V=CONR', but also with a compound of formula (1) wherein V' can be, but is not limited to, for example, OH or SH, to give A—CO—V—R—Z (14), wherein A, R and Z have the previously stated meanings whereas V can be S, O or another atom or group which can connect CO to R by chemical bonds. Likewise, a compound of formula (1) wherein V' is COOH or a reactive derivative thereof (e.g, acyl halide, ester or azide) can be reacted with a pharmaceutically active chemical entity containing a primary or secondary amino group (A—NHR'), to give compounds of the formula A—NR'—CO—R—Z (15) or, conversely, to give a compound of the formula A—CO—NR'—R—Z (16), wherein A, R, and Z have the previously stated meanings. The combination of groups, precursors, reactions and reaction conditions are easily understood by those skilled in the art in light of the discussions above. When one of the reactants or both contain other reactive groups than those needed to establish the chemical connection between A and R—Z, the interfering groups are protected by techniques established and known in the art.

The condensation reactions of the foregoing synthetic procedures are conventional in the art and are carried out under standard condensation conditions that are well known to those skilled in the art.

In addition, as mentioned previously, when the pharmaceutically active chemical entity contains a carboxylic group, it can be reacted directly with P(OH)$_3$ and PCl$_3$ as described below to yield a compound of formula A—Z (12) wherein A and Z have the previously stated meanings.

Diphosphonic acid compounds of formula V'—R—Z (1) can be synthesized by any of various methods. Treating the carboxylic group of an organic acid with phosphorous acid, P(OH)$_3$, and phosphorous trichloride, PCl$_3$, according to the method of U.S. Pat. No. 4,621,077 converts the carboxylic acid group to Z. In another method [Worms et al. (1976) In: Kosolapoff G M, Maier L (eds) Organic phosphorus compounds, vol. 7. Wiley, New York, p 1] an organic carboxylic acid of formula RCOOH, wherein R is an organic group, typically the residue of an aliphatic or aromatic carboxylic acid, optionally substituted by such groups as amino and halogen, is reacted with a mixture of water and phosphorus trichloride according to the following equation:

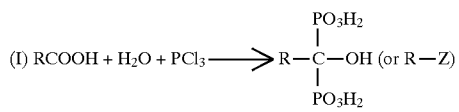

The products obtained under these anhydrous conditions are condensates, i.e., two or more molecules of the diphosphonate condensed via removal of a molecule of water. These condensates can then be converted to the compounds of formula R—Z by heating in water or in 6M HCl.

Tetraalkyl esters of gem-diphosphonic acids (R—Z, wherein R and Z have the previously stated meaning and and R$^3$ within Z is alkyl) can be prepared by the reaction of a carboxylic acid chloride with a trialkylphosphite. The resultant acylphosphonate reacts under slightly basic conditions with a dialkylphosphite to yield a diphosphonate tetraalkyl ester, which then is hydrolyzed with acid or base to the corresponding free acid. For sensitive compounds, which include most antibiotics, reaction with trimethylbromosilane inchloroform of CCl$_4$ is preferred, followed by reaction with water (no catylst).

The 1-amino-1,1-diphosphonates are made [Worms et al. (1979), Z Anorg Alig Chem 457:209–213] by reacting a nitrile or an amide with H$_3$PO$_3$ and a phosphorus trihalide and hydrolyzing the product with water, or by carrying out the reaction directly in the presence of water.

Substituting a haloacid of the formula X—(CH$_2$)$_m$—COOH (13), wherein X is Cl, Br, or I and m is an integer from 1 to 10, for RCOOH in equation (I) yields the product of formula X—(CH$_2$)$_m$—Z (14), i.e. 1, R=(CH$_2$)$_m$ which is an intermediate for preparing compounds of the present invention. Reacting a compound of formula (14) with a derivative of ammonia of the formula

wherein M is N or C, and R$^1$ and R$^2$ are independently:

1) hydrogen,
2) alkyl, preferably C$_{1-6}$alkyl
3) alkyl, preferably C$_{1-6}$alkyl substituted with one or more of OH, SH, COO halogen or primary or secondary amine, provided that at least one of R$^1$ and R$_2$ is always substituted alkyl, preferably substituted C$_{1-6}$alkyl, or
4) R$^1$ and R$^2$, taken together with the atom to which they are each attached, form a ring such as piperazine or imidazolidine, yields the compound of the formula

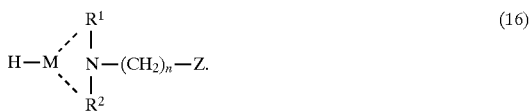

Compounds of formula (16) wherein at least one of R$^1$ and R$^2$ contains a reactive group, such as a primary or secondary amino group, a halogen atom, COOH, OH, or SH, are intermediates for use in preparing the novel pharmaceutically active chemical entities of the present invention by reaction with a pharmaceutically active compound containing a functional group which can react with the compound of formula (16).

Compounds of the formula

are prepared by using an α-amino acid as the compound of formula RCOOH in equation (I). Compounds of the formula

are prepared by using a β-amino acid as the compound of formula RCOOH in equation (I). Compounds of the formula

wherein n is from 2 to 7 are prepared by using the corresponding amino acid (for R=H this is referred to as an omega-amino acid) as the compound of formula RCOOH in equation (I). An alternative method for preparing a compound of formula (1) wherein X is 1-piperazyl is to react the corresponding compound wherein X is NH$_2$, (for example (17), (18) or (19), with bis(2-chloroethyl)amine.

Examples of some specific acids that can be converted to diphosphonates of formula R—Z according to any of the foregoing procedures are the following:

m-aminobenzoic acid, p-aminobenzoic acid, 3-chloro-4-aminobenzoic acid, 2-chloro-4-aminobenzoic acid, 2-chloro-5-aminobenzoic acid, and 3-chloro-5-aminobenzoic acid, compounds of formula (13) wherein X is Cl, Br, or I, and n=1–10, α-amino acids, e.g., alanine, aminobutyric acid, arginine, asparagine, aspartic acid, canavanine, citrulline, cysteine, cystine, dibromotyrosine, dihydroxyphenylalanine, diiodotyrosine, glutamic acid, glutamine, glycine, histidine, hydroxylysine, hydroxyproline, isoleucine, leucine, lysine, methionine, norleucine, norvaline, ornithine, phenylalanine, proline, serine, thiolhistidine, threonine, thyroxine, tryptophane, tyrosine, and valine, β-amino acids of formula RCH(NH$_2$)CH$_2$COOH wherein R is H or alkyl optionally substituted by OH, SH, and halogen, gamma-amino acids of formula RCH(NH$_2$)(CH$_2$)$_n$CH$_2$COOH wherein n is 1–10, and R is H or alkyl optionally substituted by OH, SH, and halogen.

Specific diphosphonates of formula (1) usable according to the present invention include the following:

1,2-dihydroxyethane-1,1-diphosphonic acid,
dichloromethanenediphosphonic acid (Cl$_2$MBP), difluoromethanediphosphonic acid (F₂MBP), 3-amino-1-hydroxypropane-1,1-diphosphonic acid (AHPrBP), 4-amino-1-hydroxybutane-1,1-diphosphonic acid (AHBuBP), 5-amino-1-hydroxypentane-1,1-diphosphonic acid (AHPeBP), 6-amino-1-hydroxyhexane-1,1-diphosphonic acid (AHHexBP), 3-aminophenyl-hydroxymethanediphosphonic acid, 4-aminophenyl-hydroxymethanediphosphonic acid, 2-chloro-4-aminophenyl-hydroxymethanediphosphonic acid, 3-chloro-4-aminophenyl-hydroxymethanediphosphonic acid, 2-chloro-5-aminophenyl-hydroxymethanediphosphonic acid, 3-chloro-5-aminophenyl-hydroxymethanediphosphonic acid, 2-(4-aminophenyl)-1-hydroxyethane-1,1-diphosphonic acid, 3-(2-chloro-4-aminophenyl-1-hydroxypropane-1,1-diphosphonic acid, 4-(2-chloro-5-aminophenyl)-1-hydroxybutane-1,1-diphosphonic acid, 5-(3-chloro-5-aminophenyl)-1-hydroxypentane-1,1-diphosphonic acid, 2-bromo-1-hydroxy-1,1-ethanediphosphonic acid, 3-fluoro-1-hydroxy-1,1-propanediphosphonic acid, 4-chloro-1-hydroxy-1,1-butanediphosphonic acid, 5-bromo-1-hydroxy-1,1-pentanediphosphonic acid, 6-fluoro-1-hydroxy-1,1-hexanediphosphonic acid, 7-chloro-1-hydroxy-1,1-heptanediphosphonic acid, 8-bromo-1-hydroxy-1,1-octanediphosphonic acid, 9-fluoro-1-hydroxy-1,1-nonanediphosphonic acid, 10-chloro-1-hydroxy-1,1-decanediphosphonic acid, 2-amino-1-hydroxy-1,1-ethanediphosphonic acid, 3-amino-1-hydroxy-1,1-propanediphosphonic acid, 4-amino-1-hydroxy-1,1-butanediphosphonic acid, 5-amino-1-hydroxy-1,1-pentanediphosphonic acid, 6-amino-1-hydroxy-1,1-hexanediphosphonic acid, 7-amino-1-hydroxy-1,1-heptanediphosphonic acid, 8-amino-1-hydroxy-1,1-octanediphosphonic acid, 9-amino-1-hydroxy-1,1-nonanediphosphonic acid, 10-amino-1-hydroxy-1,1-decanediphosphonic acid, (1-piperazyl)-hydroxymethanediphosphonic acid, 2-(1-piperazyl)-1-hydroxy-1,1-ethanediphosphonic acid, 3-(l-piperazyl)-1-hydroxy-1,1-propanediphosphonic acid, 4-(1-piperazyl)-1-hydroxy-1,1-butanediphosphonic acid, or 5-(1-piperazyl)-1-hydroxy-1,1-pentanediphosphonic acid.

Also usable according to the present invention are the esters of the diphosphonic acids listed above.

Reaction of a compound of formula Z-R-NH₂ or

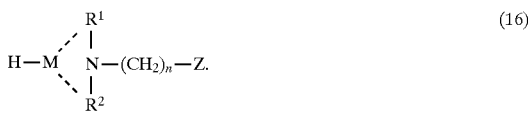

with a halogen-containing pharmaceutically active chemical entity results in the formation of hydrogen halide and bonding of the Z-containing moiety to the chemical entity.

Pharmaceutically active chemical entities containing groups capable of reacting with the V'-substituent of the diphosphonates of formula (1), namely, carboxyl group or derivative thereof (e.g., acyl halide, ester, azide), primary and secondary amino group, hydroxyl, and halogen (Cl, Br and I) are useful according to the present invention. Consequently, examples of useful pharmaceutically active chemical entities include, without intending to be limiting thereto, aminoglycosides such as amikacin (U.S. Pat. No. 3,781,268), apramycin (U.S. Pat. No. 3,691,279), arbekacin (U.S. Pat. No. 4,107,424), bambermycin (U.S. Pat. No. 3,674,866), butirosin (U.S. Pat. No. 3,541,078), dibekacin (German patent 2,135,191), dihydrostreptomycin (U.S. Pat. No. 2,498,574), fortimycin A (U.S. Pat. No. 3,976,768) and fortimycin B (Japan Kokai 75 145,588), gentamicin (U.S. Pat. Nos. 3,091,572 and 3,136,704), isepamicin (Belgian patent 818,431), kanamycin (U.S. Pat. No. 2,931,798), micronomicin (German patent 2,326,781), neomycin (2,799,620), neomycin undecylenate (U.S. Pat. No. 3,022,286), netilmicin (German patent 2,437,160), paromomycin (U.S. Pat. No. 2,916,485), ribostamycin (German patent 1,814,735), sisomicin (U.S. Pat. No. 3,832,286), spectinomycin (U.S. Pat. No. 3,234,092), streptomycin (U.S. Pat. No. 2,868,779), streptonicozid (Pennington et al., *J. Am. Chem. Soc.* 75, 2261 (1953) and tobramycin (Stark et al., Higgens, Kastner; Thompson, Presti; Wick, Welles, *Antimicrob. Ag. Chemother.,* 1967, 314–348;

amphenicols such as azidamfenicol (U.S. Pat. No. 2,882,275), chlorampphenicol [Bartz, *J. Biol. Chem.* 172, 445 (1948)], chloramphenicol palmitate (U.S. Pat. No. 2,662,906), chloramphenicol pantothenate (U.S. Pat. No. 3,078,300), florfenicol (U.S. Pat. No. 4,235,892) and thiamphenicol [Cutler et al., *J. Am. Chem. Soc.* 74, 5475 (1952)];

ansamycins such as rifamide (U.S. Pat. No. 3,313,804);

carbapenems, for example, imipenem (U.S. Pat. No. 4,194,047);

cephalosporins, for example, cefaclor (U.S. Pat. No. 3,925,372), cephadroxil U.S. Pat. No. 3,816,253), cefamandole U.S. Pat. No. 3,641,021), cefatrizine (U.S. Pat. No. 3,970,651), cefazedone (German patent 2,345,402), cefazolin (U.S. Pat. No. 3,516,997), cefixime (U.S. Pat. No. 4,409,214), cefmenoxime (U.S. Pat. No. 4,098,888), cefodizime (U.S. Pat. No. 4,278,793), cefonicid (U.S. Pat. No. 4,093,723), cefoperazone (U.S. Pat. No. 4,410,5220, ceforanide (U.S. Pat. No. 4,172,196), cefotaxime (U.S. Pat. No. 4,098,888), cefotiam (German patent 2,607,064), cefpimizole (U.S. Pat. No. 4,217,450), cefpiramide (Belgian patent 833,063), cefpodoxime proxetil (U.S. Pat. No. 4,486,425), cefroxidine (U.S. Pat. No. 4,073,902), cefsulidin, (U.S. Pat. No. 4,065,619), ceftazidime (U.S. Pat. No. 4,258,041), cefteram (Belgian patent 890,499), ceftozole (U.S. Pat. No. 3,516,997), ceftibuten (U.S. Pat. No.

4,634,697), ceftizoxime (U.S. Pat. No. 4,427,674), ceftriaxone (U.S. Pat. No. 4,327,210), cefuroxime (U.S. Pat. No. 3,974,153), cefuzonam (U.S. Pat. No. 4,399,132), cephalexin (U.S. Pat. No. 3,275,626), cephaloglycin (U.S. Pat. No. 3,422,103), cephaloridine (French patent 1,384,197), cephalosporin C (U.S. Pat. No. 3,082,155), cephalothin (French patent 1,384,197), cephapirin sodium (U.S. Pat. No. 3,422,100), cephradine (U.S. Pat. No. 3,485,819) and pivecfalexin (German patent 1,951,012);

cephamycins such as cefbuperazone (U.S. Pat. No. 4,263,292), cefmetazole (U.S. Pat. No. 4,007,177), cefminox (U.S. Pat. No. 4,357,331), cefotetan (U.S. Pat. No. 4,263,432) and cefoxitin (U.S. Pat. No. 4,297,488);

monobactams such as aztreonam (Netherlands patent application 8,100,571, carumonam (U.S. Pat. No. 4,572,801), and tigemonam (U.S. Pat. No. 4,638,061);

oxacephems such as flomoxef (U.S. Pat. No. 4,532,233) and moxalactam (U.S. Pat. No. 4,138,486);

penicillins such as amdinocillin (U.S. Pat. No. 3,957,764, amoxicillin (U.S. Pat. No. 3,192,198) ampicillin (U.S. Pat. No. 2,985,648), carbenicillin (U.S. Pat. No. 3,142,673), clometocillin (U.S. Pat. No. 3,007,920), cloxacillin (Doyle et al., *J. Chem. Soc.* 1963, 5838), cyclacillin (U.S. Pat. No. 3,194,802), dicloxacillin (U.S. Pat. No. 3,239,507), epicillin (U.S. Pat. No. 3,485,819), floxacillin (U.S. Pat. No. 3,239,507), hetacillin (U.S. Pat. No. 3,198,804), lenampicillin (U.S. Pat. No. 4,342,693), metampicillin (Belgian patent 661,232), oxacillin (U.S. Pat. No. 2,996,501), penicillin V (Brandl et al., *Wien. Med. Wochenschr.* 1953, 602), piperacillin (U.S. Pat. No. 4,087,424), pivampicillin ((U.S. Pat. No. 3,660,575), propicillin (British patent 877,120), sulbenicillin (U.S. Pat. No. 3,660,379) and ticarcillin (U.S. Pat. No. 3,282,926);

lincosamides such as clindamycin (U.S. Pat. No. 3,475,407) and lincomycin (U.S. Pat. Nos. 3,086,912 and 3,155,580);

macrolides such as azithromycin (U.S. Pat. No. 4,517,359), carbomycin (U.S. Pat. No. 2,960,438), clarithromycin (U.S. Pat. No. 4,331.803), erythromycin (U.S. Pat. No. 2,823,203), josamycin (Japanese patent 66 21,759), leucomycins (U.S. Pat. No. 3,535,309), midecamycins (U.S. Pat. No. 3,761,588), miokamycin (Japanese Kokai 74 124087), oleandomycin (U.S. Pat. Nos. 2,757,123 and 2,842,481), primycin (U.S. Pat. No. 3,498,884), rokitamycin (German patent 2,918,954), rosaramicin (S. African patent 71 00,402), roxithromycin (U.S. Pat. No. 4,359,545), spiramycin (U.S. Pat. No. 2,943,023), and troleandomycin (British patent 877,730);

polypeptides such as bacitracin (U.S. Pat. No. 2,915,432), capreomycin (U.S. Pat. No. 3,143,468), colistin (Japanese patent 57 4898), enduracidin (British patent 1,163,270), enviomycin (U.S. Pat. No. 3,892,732), gramicidin (U.S. Pat. No. 2,534,541), mikamycin (French patent 1,349,946), polymyxin (U.S. Pat. No. 2,565,057), polymyxin B-methanesulfonic acid (U.S. Pat. No. 3,044,934), pristinamycin (U.S. Pat. No. 3,154,475), ristocetin (U.S. Pat. No. 2,990,329), Teicoplanin (U.S. Pat. No. 4,239,751), thiostrepton (U.S. Pat. Nos. 2,982,689 and 2,982,698), tuberactinomycin (U.S. Pat. No. 3,639,580), tyrocidine (U.S. Pat. No. 3,265,572), tyrothricin, vancomycin (U.S. Pat. No. 3,067,099), viomycin (U.S. Pat. No. 2,633,445), virginiamycin, and zinc bacitracin (U.S. Pat. No. 2,803,584);

tetracyclines such as apicycline (Netherlands patent application 6,515,688), chlortetracycline (U.S. Pat. No. 2,482,055), clomocycline (Belgian patent 628,142), demeclocycline (U.S. Pat. No. 2,878,289), doxycycline (U.S. Pat. No. 3,200,149), guamecycline (British patent 1,042,207), lymecycline (U.S. Pat. No. 3,043,716), meclocycline 2,984,686), methacycline (U.S. Pat. No. 3,026,354), minocycline (U.S. Pat. Nos. 3,148,212 and 3,226,436), oxytetracycline (U.S. Pat. No. 2,516,080), penimepicycline (British patent 897,826), pipacycline (British patent 888,968), rolitetracycline (U.S. Pat. No. 3,104,240), sancycline (U.S. Pat. No. 3,019,260), senociclin (U.S. Pat. No. 3,218,335), and tetracycline (U.S. Pat. No. 2,699,054);

cycloserine (U.S. Pat. No. 2,773,878), doxorubicin (U.S. Pat. No. 3,590,028), and mupirocin (U.S. Pat. No. 3,977,943);

2,4-diaminopyrimidines such as brodimoprim (U.S. Pat. No. 4,024,145), tetroxoprim (U.S. Pat. No. 3,992,379), and trimethoprim (US patent 3,049,544);

nitrofurans such as furazolium chloride (U.S. Pat. No. 3,169,970), nifuradene (U.S. Pat. No. 2,746,960), nifurprazine (British patent 966,832), nifurtoinol (U.S. Pat. No. 3,446,802), and nitrofurantoin (U.S. Pat. No. 2,610,181);

quinolones and analogs such as amifloxacin (U.S. Pat. No. 4,499,091), cinoxacin (U.S. Pat. No. 3,669,965), ciprofloxacin (U.S. Pat. No. 4,670,444), difloxacin (U.S. Pat. No. 4,730,000), enoxacin (U.S. Pat. No. 4,359,578), fleroxacin (U.S. Pat. No. 4,398,029), flumequine (U.S. Pat. No. 3,896,131), lomefloxacin (U.S. Pat. No. 4,528,287), miloxacin (U.S. Pat. No. 3,799,930), nalidixic acid (U.S. Pat. No. 3,149,104), norfloxacin (U.S. Pat. No. 4,146,719), ofloxacin (U.S. Pat. No. 4,382,892), oxolinic acid (U.S. Pat. No. 3,287,458), pefloxacin (U.S. Pat. No. 4,292,317), pipemidic acid (U.S. Pat. No. 3,887,557), piromidic acid (British patent 1,129,358), rosoxacin (U.S. Pat. No. 3,753,993), sparfloxacin (*Antimicrobial Agents & Chemotherapy* 1989, 33, 1167–1173) and tosufloxacin (U.S. Pat. No. 4,704,459);

sulfonamides such as acetyl sulfamethoxypyrazine (U.S. Pat. No. 3,098,069), acetyl sulfisoxazole (U.S. Pat. No. 2,721,200), azosulfamide (U.S. Pat. Nos. 2,123,634 and 2,148,910), benzylsulfamide, chloramine-B, chloramine-T, dichloramine T (U.S. Pat. No. 2,495,489), formosulfathizale [Druey et al., *Helv. Chim. Acta* 31, 2184 (1948)], $N^2$-formylsulfisomidine (German patents 1,122,511 and 1,126,857), $N^4$-$\beta$-D-glucosylsulfanilamide [Kuhn et al., Ber. 71, 621 (1938)], mafenide (U.S. Pat. No. 2,288,531), 4'-(methylsulfamoyl)sulfanilanilide (French patent 817,034), p-nitrosulfathiazole (U.S. Pat. No. 2,443,742), norprylsulfamide (U.S. Pat. No. 2,262,544), phthalylsulfacetamide [(Basu, *J. Indian Chem. Soc.* 26, 130 (1949)], phthalylsulfathiazole (U.S. Pat. Nos. 2,324,013 and 2,324,015), salazosulfadimidine [Korkuczanski, *Przem. Chem.* 37, 162 (1958)], succinylsulfathiazole (U.S. Pat. Nos. 2,324,013 and 2,324,014), sulfabenzamide (U.S. Pat. No. 2,240,496), sulfacetamide (U.S. Pat. No. 2,411,495, sulfachlorpyridazine (U.S. Pat. No. 2,790,798), sulfachrysoidine [Gley et al., *Compt. Rend. Soc. Biol.* 125, 1027 (1937)], sulfacytine (U.S. Pat. No. 3,375,247), sulfadiazine (U.S. Pat. No. 2,407,966), sulfadicramide (U.S. Pat. No. 2,417,005), sulfadimethoxine (U.S. Pat.

No. 2,703,800), sulfadoxine (U.S. Pat. No. 3,132,139), sulfaethidole [Wojahn et al., *Arch. Pharm.,* 284, 53 (1951)], sulfaguanidine (U.S. Pat. Nos. 2,218,490, 2,229,784 and 2,233,569), sulfaguanole (U.S. Pat. No. 3,562,258), sulfalene (U.S. Pat. No. 3,098,069), sulfaloxic acid (German patent 960,190), sulfamerazine (U.S. Pat. No. 2,407,966), sulfameter (U.S. Pat. No. 3,214,335), sulfamethazine (U.S. Pat. No. 2,407,966), sulfamethizole (U.S. Pat. No. 2,447,702), sulfamethomidine (German patent 926,131), sulfamethoxazole (U.S. Pat. No. 2,888,455), sulfamethoxypyridazine (U.S. Pat. No. 2,712,012), sulfametrole (U.S. Pat. No. 3,247,193), and sulfamidochrysoidine (U.S. Pat. No. 2,085,037);

sulfones such as acedapsone [Fromm et al., Ber, 41, 2270 (1908)], acediasulfone [Jackson, *J. Am. Chem. Soc.* 70, 680 (1948)], acetosulfone sodium (U.S. Pat. No. 2,358, 365), dapsone (French patent 829,926), diathymosulfone (British patent 758,744), glucosulfone sodium (Swiss patent 234,108), solasulfone (British patent 491, 265), succisulfone (U.S. Pat. No. 2,268,754), sulfonilic acid, p-sulfanilylbenzylamine (Dewing, *J. Chem. Soc.* 1946, 466), p,p'-sulfonyldianiline-N,N'-digalactoside, sulfoxone sodium (U.S. Pat. No. 2,256,575), and thiazolsulfone (2,389,126);

others such as clofoctol (U.S. Pat. No. 3,830,852), hexedine (U.S. Pat. No. 3,357,886), nitroxoline [Kostanecki, *Ber.* 24, 154 1891)], xibornol (British patent 1,206,774); hydnocarpic acid [Diaper et al., *Biochem J.* 42, 581 (1948)], p-amino-salicylic acid (U.S. Pat. No. 427,564), p-aminosalicylic acid hydrazide (Spanish patent 206,645), benzoylpas (British patent 676,363), 5-bromosalicylhydroxamic acid (Urbanski et al., *Nature* 170, 753 (1952), capreomycin (U.S. Pat. No. 3,143,468), clofazimine (Barry et al., *Nature* 179, 1013 (1957), cyacetacide (U.S. Pat. No. 2,849,369), dihydrostreptomycin (U.S. Pat. No. 2,498, 574), enviomycin (U.S. Pat. No. 3,892,732), ethambutol [Wilkinson et al., *J. Am. Chem. Soc.* 83, 2212 (1961)], ethionamide (British patent 800,250), 4'-formylsuccinanilic acid (German patent 852,086), furonazide [Miyatake et al. *J. Pharm. Soc. Japan* 75, 1066, (1955)], glyconiazide (U.S. Pat. No. 2,940,899), isobutol (U.S. Pat. No. 3,718,655), isonizid (U.S. Pat. No. 2,830,994), isoniazid methanesulfonate (U.S. Pat. No. 2,759,944), morphazinzmide (German patent 1,129,492), opiniazide [Pershin et al., C.A. 51, 10747e (1957)], pasiniazide (Swiss patent 303,085), phenyl aminosalicylate (U.S. Pat. No. 2,604,488), protionamide (British patent 800,250), pyrazinamide (German patent 632,257), rifampin (U.S. Pat. No. 3,342,810), salinizid [Hart et al., *Antibot. & Chemother.* 4, 803 (1954)], subathizone [Bernstein et al., *J. Am. Chem. Soc.* 73, 906 (1951), sulfoniazide (U.S. Pat. No. 2,727, 041), thiacetazone [Domagk et al., *Naturwiss* 33, 315 (1946)], tiocarlide (U.S. Pat. No. 2,703,815), tuberactinomycin (U.S. Pat. No. 3,639,580), tubercidin [Anzai et al., J. Antiobot. 10A, 201 (1957)], tuberin (Japanese patent 64 7399), verazide [Fox et al., *J. Org. Chem.* 18, 983 (1953), viomycin (U.S. Pat. No. 2,633,445), and viomycin pantothenate (German patents 954,874 and 1,011,800).

Synthesis of Intermediates

2-Amino-1-hydroxyalkane-1,1-diphosphonic acids can be prepared following the procedure of Example 1 of U.S. Pat. No. 4,621,077 except substituting for the 5-aminovaleric acid of that example an equivalent amount of the acid of column 1 thereby yielding the diphosphonic acid compound of column 2:

| 1 | 2 |
|---|---|
| glycine | 2-amino-1-hydroxyethane-1,1-diphosphonic acid |
| alanine | 2-amino-1-hydroxypropane-1,1-diphosphonic acid |
| β-alanine | 3-amino-1-hydroxypropane-1,1-diphosphonic acid |
| 4-aminobutyric acid | 4-amino-1-hydroxybutane-1,1-diphosphonic acid |
| 5-aminopentanoic acid | 5-amino-1-hydroxypentane-1,1-diphosphonic acid |
| 6-aminocaproic acid | 6-amino-1-hydroxyhexane-1,1-diphosphonic acid |

(Aminophenyl)-hydroxymethanediphosphonic acids are prepared by employing an aminobenzoic acid of column 1 in equation I, supra, to yield the compound of column 2:

| 1 | 2 |
|---|---|
| 2-aminobenzoic acid | (2-aminophenyl)-hydroxymethane-diphosphonic acid |
| 3-aminobenzoic acid | (3-aminophenyl)-hydroxymethane-diphosphonic acid |
| 4-aminobenzoic acid | (4-aminophenyl)-hydroxymethane-diphosphonic acid |
| 2-fluoro-3-aminobenzoic acid | (2-fluoro-3-aminophenyl)-hydroxymethane-diphosphonic acid |
| 2-fluoro-4-aminobenzoic acid | (2-fluoro-4-aminophenyl)-hydroxymethane-diphosphonic acid |
| 2-fluoro-5-aminobenzoic acid | (2-fluoro-5-aminophenyl)-hydroxymethane diphosphonic acid |
| 3-fluoro-4-aminobenzoic acid | (3-fluoro-4-aminophenyl)-hydroxymethane-diphosphonic acid |
| 3-fluoro-5-aminobenzoic acid | (3-fluoro-5-aminophenyl)-hydroxymethane-diphosphonic acid |
| 2-chloro-3-aminobenzoic acid | (2-chloro-3-aminophenyl)hydroxy methane-diphosphonic acid |
| 2-chloro-4-aminobenzoic acid | (2-chloro-4-aminophenyl)-hydroxymethane-diphosphonic acid |
| 2-chloro-5-aminobenzoic acid | (2-chloro-5-aminophenyl)-hydroxymethane-diphosphonic acid |
| 2-amino-3-chlorobenzoic acid | (2-amino-3-chlorophenyl)-hydroxymethane-diphosphonic acid |
| 3-chloro-4-aminobenzoic acid | (3-chloro-4-aminophenyl)-hydroxymethane-diphosphonic acid |
| 3-chloro-5-aminobenzoic acid | (3-chloro-5-aminophenyl)-hydroxymethane-diphosphonic acid |
| 2-trifluoromethyl-3-amino benzoic acid | (2-trifluoromethyl-3-aminophenyl)-hydroxymethanediphosphonic acid |
| 2-trifluoromethyl-4-amino-benzoic acid | (2-trifluoromethyl-4-aminophenyl)-hydroxymethanediphosphonic acid |
| 2-trifluoromethyl-5-amino-benzoic acid | (2-trifluoromethyl-5-aminophenyl)-hydroxymethanediphosphonic acid |
| 3-trifluoromethyl-4-amino-benzoic acid | (3-trifluoromethyl-4-aminophenyl)-hydroxymethanediphosphonic acid 3-(3-trifluoromethyl-5-aminophenyl)-hydroxymethanediphosphonic acid |
| trifluoromethyl-5-amino-benzoic acid | |

The compounds of the present invention are intended for treatment of a member of a mammalian species, e.g., dogs, mice, primates and humans, and normally are administered orally but also can be administered by injection. For oral administration, the compounds can be used at a dosage amount that, in general, is less than that at which the pharmaceutically active component itself is employed. The compounds of the present invention are used in the form of various pharmaceutical preparations such as tablets, capsules, powders, granules, syrups and the like which are well known in the art, and which can be prepared by methods known per se using suitable diluents, bindings, disintegrators, coating agents and the like. Other preparations suitable for injection can also be prepared by techniques known in the art.

The following examples illustrate the present invention without, however, limiting the same thereto.

EXAMPLE 1

9-Fluoro-3-methyl-10-{4-[4-hydroxy-4,4-bis (dimethoxyphospphono)-1-butyl]-1-piperazyl}-7-oxo-2,3-dihydro-7H-pyrido[1,2,3-de][1,4] benzoxazine-6-carboxylic acid 4-Chloro-1-hydroxy-1,1-butanediphosphonic acid is prepared by treating 4-chlorobutanoic acid either with phosphorous acid and phosphorus trichloride as described in U.S. Pat. No. 4,621,077, or by treatment with phosphorus trichloride and methanesulfonic acid, as described in U.S. Pat. No. 4,922,007. The acid is converted to the tetramethyl ester by reaction with trimethyl orthoformate (Nicholson et al., J. Org. Chem. 1970, 35, 3149) and the ester is then reacted with piperazine to yield 4-(1-piperazyl)-1-hydroxy-1,1-butanediphosphonic acid tetramethyl ester. (An alternative synthesis is to react 4-amino-1-hydroxy-1,1-butanediphosphonic acid tetramethyl ester with bis-(2-chloroethyl)amine.) 9,10-Difluoro-3-methyl-7-oxo-2,3-dihydro-7H-pyrido[1,2,3-de][1,4]benzoxazine-6-carboxylic acid is prepared following the procedure of example 2 of U.S. Pat. No. 4,382,892. The 6-carboxylic acid is then subjected to the procedure of example 3 of U.S. Pat. No. 4,382,892 except substituting for N-methylpiperazine an equivalent amount of 4-(1-piperazyl)-1-hydroxy-4,4-butanediphosphonic acid tetramethyl ester. The crude product gives after extraction, solvent evaporation and recrystallization 9-fluoro-3-methyl-10-{4-[4-hydroxy-4,4-bis (dimethoxyphosphono)-1-butyl]-1-piperazyl}-7-oxo-2,3-dihydro-7H-pyrido[1,2,3-de][1,4]benzoxazine-6-carboxylic acid.

EXAMPLE 2

9-Fluoro-10-{4-[3-hydroxy-3,3-bis (dimethoxyphosphono)-1-propyl]-1-piperazyl}-7-oxo-2,3-dihydro-7H-pyrido-[1,2,3-de][1,4] benzoxazine-6-carboxylic acid The tetramethyl ester of 3-chloro-1-hydroxy-1,1-propanediphosphonic acid is reacted with sodium azide and forms tetramethyl 3-azido-1-hydroxypropane-1,1-diphosphonate, which is hydrogenated over Pt at room temperature under 1 bar of hydrogen to tetramethyl 3-amino-1-hydroxy-1,1-propanediphosphonate. 9,10-Difluoro-7-oxo-2,3-dihydro-7H-pyrido[1,2,3-de][1,4]-benzoxazine-6-carboxylic acid is prepared according to the procedure of example 1 of U.S. Pat. No. 4,382,892. The acid is then employed in the procedure of example 7 of the cited patent except substituting for methyl hydrazine an equivalent amount of 3-(1-piperazyl)-1-hydroxy-1,1-propanediphosphonic acid tetramethyl ester, prepared by reaction of 3-amino-1-hydroxy-1,1-propanediphosphonic acid tetramethyl ester with bis-(2-chloroethyl)-amine, to yield 9-fluoro-10-{4-[3-hydroxy-3,3-bis (dimethoxyphosphono)-1-propyl]-1-piperazyl}-7-oxo-2,3-dihydro-7H-pyrido-[1,2,3-de][1,4] benzoxazine-6-carboxylic acid.

Capsules suitable for oral administration are prepared from the following formulation in known manner:

| | |
|---|---|
| 9-fluoro-10-[4-(3-hydroxy-3,3-diphosphono-1-propyl)-1-piperazyl]-7-oxo-2,3-dihydro-7H-pyrido[1,2,3-de][1,4]-benzoxazine-6-carboxylic acid | 100.0 mg |
| CMC calcium | 23.0 mg |
| Corn starch | 22.5 mg |
| Magnesium stearate | 1.5 mg |

EXAMPLE 3

9-Chloro-3-methyl-10-{4-[2-hydroxy-2,2-bis (dimethoxyphosphono)ethyl]-1-piperazyl}-7-oxo-2, 3-dihydro-7H-pyrido[1,2,3-de][1,4]-benzoxazine-6-carboxylic acid 9-Chloro-10-fluoro-3-methyl-7-oxo-2,3-dihydro-7H-pyrido[1,2,3-de][1,4]benzoxazine-6-carboxylic acid is prepared according to the procedure of example 8 of U.S. Pat. No. 4,382,892. The acid then is employed in the procedure of example 3 of the cited patent except substituting for N-methylpiperazine an equivalent amount of 1-[2-hydroxy-2,2-bis(dimethoxyphosphono)ethyl]-piperazine to yield 9-chloro-3-methyl-10-{4-[2-hydroxy-2,2-bis (dimethoxyphosphono)ethyl]-1-piperazyl}-7-oxo-2,3-dihydro-7H-pyrido[1,2,3-de][1,4]-benzoxazine-6-carboxylic acid.

EXAMPLE 4

9-Fluoro-3-methyl-10-{4-[2-hydroxy-2,2-bis (dimethoxyphosphono)ethyl]-1-piperazyl}-7-oxo-2, 3-dihydro-7H-pyrido[1,2,3-de][1,4]benzoxazine-6-carboxylic acid The procedure of example 3 of U.S. Pat. No. 4,382,892 is repeated except substituting for N-methylpiperazine an equivalent amount of tetramethyl 2-(1-piperazyl)-1-hydroxy-1,1-ethanediphosphonate, prepared by the reaction of Cl—(CH$_2$)—Z (2-chloro-1-hydroxy-1,1-ethane-diphosphonic acid, tetramethyl ester) and piperazine, to yield the title compound.

EXAMPLE 5

9-Fluoro-3-methyl-10-[3-hydroxy-3,3-bis (dimethoxyphosphono)-1-propylamino]-7-oxo-2,3-dihydro-7H-pyrido[1,2,3-de][1,4benz-oxazine-6-carboxylic acid 9,10-Difluoro-3-methyl-7-oxo-2,3-dihydro-7H-pyrido[1, 2,3-de][1,4]benzoxazine-6-carboxylic acid, prepared according to the procedure of example 1 of U.S. Pat. No. 4,382,892, is reacted with 3-hydroxy-3,3-bis (dimethoxyphosphono)-1-propylamine and a quantity of base sufficient to neutralize the acid groups of both reactants and the acid formed in the reaction, thus yielding 9-fluoro-3-methyl-10-[3-hydroxy-3,3-bis(dimethoxyphosphono)-1-propylamino]-7-oxo-2,3-dihydro-7H-pyrido[1,2,3-de](1,4] benzoxazine-6-carboxylic acid.

EXAMPLE 6

9-Fluoro-3-[hydroxy-bis(diethoxyphosphono) methyl]-10-(4-methyl-1-piperazyl)-7-oxo-2,3-dihydro-7H-pyrido[1,2,3-de][1,4]benzoxazine-6-carboxylic acid 3.9 g of 2,3-difluoro-6-nitrophenol and 3.0 g of chloro-pyruvic acid are reacted as described for chloroacetone in Example 8 of U.S. Pat. No. 4,382,892, to yield (2,3-difluoro-6-nitrophenoxy)-pyruvic acid. Catalytic hydrogenation (Pd/C or Raney Ni, room temperature) of the product yields in one step 7,8-difluoro-[1,4]benzoxazine-3-carboxylic acid, which is converted to its acid chloride and then is reacted first with triethylphosphite and next with diethylphosphite and a base, to form 7,8-difluoro-3-[hydroxy-bis (diethoxyphosphono)methyl]-[1,4]benzoxazine. Condensation of the latter with diethyl ethoxymethylidenemalonate, as in the above-mentioned patent, cyclization, and ester hydrolysis gives 9,10-difluoro-3-[hydroxy-bis (diethoxyphosphono)methyl]-7-oxo-2,3-dihydro-7H-pyrido [1,2,3-de][1,4]benzoxazine-6-carboxylic acid, which is finally reacted with 1-methylpiperazine to yield 9-fluoro-3-[hydroxy-bis(diethoxyphosphono)methyl]-10-(4-methyl-l-piperazyl)-7-oxo-2,3-dihydro-7H-pyrido[1,2,3-de][1,4] benzoxazine-6-carboxylic acid.

EXAMPLE 7

9-Fluoro-3-methyl-6-[hydroxy-bis (diethoxyphosphono)methyl]-10-(4-methyl-1-piperazyl)-7-oxo-2,3-dihydro-7H-pyrido[1,2,3-de][1,4]-benzoxazine 9-Fluoro-3-methyl-10-(4-methyl-1-piperazinyl)-7-oxo-2,3-dihydro-7H-pyrido[1,2,3-de][1,4]benzoxazine-6-carboxylic acid, which is prepared according to the procedure of example 3 of U.S. Pat. No. 4,382,892, is reacted with phosphorous acid and phosphorous trichloride as shown in Example 6, supra, and gives 9-fluoro-3-methyl-6-(hydroxydiphosphono-methyl)-10-(4-methyl-1-piperazyl)-7-oxo-2,3-dihydro-7H-pyrido[1,2,3-de][1,4]benzoxazine.

EXAMPLE 8

6-Chloro-1-ethyl-7-{4-[3-hydroxy-3,3-bis (dimethoxyphosphono)-1-propyl]-1-piperazyl}-4-oxo-1,4-dihydroquinoline-3-carboxylic acid 6,7-Dichloro-1-ethyl-(4-oxo-1,4-dihydroquinoline-3-carboxylic acid is prepared according to the procedure of U.S. Pat. No. 4,292,317. The acid is then employed in the procedure of example 31 of the cited patent except substituting for 1-methyl hydrazine an equivalent amount of 1-[3-hydroxy-3,3-bis(dimethoxyphosphono)-1-propyl]-piperazine to yield 6-chloro-1-ethyl-7-{4-[3-hydroxy-3,3-bis(dimethoxyphosphono)-1-propyl]-1-piperazyl}-4-oxo-1,4-dihydroquinoline-3-carboxylic acid.

For oral administration, suitable forms of administration are, for example, compressed tablets, capsules, pills and suspensions. The solid forms preferably contain at least 100 mg of 6-chloro-1-ethyl-7-{4-[3-hydroxy-3,3-bis (dimethoxyphosphono)-1-propyl]-1-piperazyl}]-4-oxo-1,4-dihydroquinoline-3-carboxylic acid. Suitable carriers for such solid forms are, for example, lactose, starch, talc, gelatin and magnesium stearate. Aqueous forms preferably contain at least 20 mg of the active compound per ml. Water soluble high molecular weight compounds such as, for example, cellulose esters and polyethylene glycols, may be included in such suspensions as stabilizers. Sweetening agents, aromatising agents and/or colorants also may be added.

EXAMPLE 9

6-Fluoro-l-methyl-7-[4-hydroxy-4,4-bis (dimethoxyphosphono)-1-butylamino]-4-oxo-1,4-dihydroquinoline-3-carboxylic acid 7-Chloro-6-fluoro-1-methyl-4-oxo-1,4-dihydro-quinoline-3-carboxylic acid is prepared according to the procedure of U.S. Pat. No. 4,292,317. The acid is then employed in the procedure of example 32 of the cited patent except substituting for piperazine an equivalent amount of $H_2N—(CH_2)_3—Z$ (4-amino-1-hydroxy-butane-1,1-diphosphonic acid, tetramethyl ester) to yield 6-fluoro-1-methyl-7-[4-hydroxy-4,4-bis(dimethoxyphosphono)-1-butylamino]-4-oxo-1,4-dihydroquinoline-3-carboxylic acid.

Injectable compositions preferably comprise solutions containing at least 200 mg of the active compound per 5 or 10 ml of final solution. If desired the solution may contain the necessary amount of NaCl to render the solution isotonic. The solutions can be presented in 5 or 10 ml ampoules which are sterilized in an autoclave. Equally, after sterile filtration, 5 or 10 ml of the solution can be filled into the appropriate sized sterile ampoules and then subjected to lyophilization.

EXAMPLE 10

6-Chloro-1-ethyl-3-(hydroxy-diphosphonomethyl)-7-(4-methyl-1-piperazyl)-4-oxo-1,4-dihydroquinoline and its tetraethyl ester 6-Chloro-1-ethyl-7-(4-methyl-1-piperazyl)-4-oxo-1,4-dihydroquinoline-3-carboxylic acid is prepared according to the procedure of U.S. Pat. No. 4,292,317. The acid then is reacted with $P(OH)_3$ and $PCl_3$ as shown in Example 1, supra, to afford 6-chloro-1-ethyl-3-(hydroxy-diphosphonomethyl)-7-(4-methyl-1-piperazyl)-4-oxo-1,4-dihydroquinoline. Alternatively, the carboxylic acid group is converted to the acid chloride and then is reacted first with triethylphosphite and next with diethylphosphite and a base, to form the tetraethyl ester of the title compound.

EXAMPLE 11

6-Chloro-7-[6-hydroxy-6,6-bis (dimethoxyphosphono)-1-hexylamino]-1-methyl-4-oxo-1,4-dihydroquinoline-3-carboxylic acid 6,7-Dichloro-1-methyl-4-oxo-1,4-dihydro-quinoline-3-carboxylic acid is prepared according to the procedure of U.S. Pat. No. 4,292,317. The acid is then employed in the procedure of example 17 of the cited patent except substituting for piperazine an equivalent amount of $H_2N—(CH_2)_5—Z$ (tetramethyl 6-amino-1-hydroxy-1,1-hexanediphosphonate) to yield 6-fluoro-7-(6-hydroxy-6,6-bis(dimethoxyphosphono)-1-hexylamino]-1-methyl-4-oxo-1,4-dihydroquinoline-3-carboxylic acid.

EXAMPLE 12

6-Fluoro-1-(3-hydroxy-3,3-diphosphono-1-propyl)-7-(-4-methyl-1-piperazyl)-4-oxo-1,4-dihydroquinoline-3-carboxylic acid 7-Chloro-3-ethoxycarbonyl-6-fluoro-4-oxo-1,4-dihydroquinoline is reacted with $Cl—(CH_2)_2—Z$ (3-chloro-1-hydroxy-1,1-propanediphosphonic acid, tetramethyl ester) following the procedure of U.S. Pat. No. 4,292,317 and gives 7-chloro-3-ethoxycarbonyl-6-fluoro-1-[3-hydroxy-3, 3-bis(dimethoxyphosphono)-1-propyl]-4-oxo-1,4-dihydroquinoline which, in turn, is treated with 1-methylpiperazine to yield 3-ethoxycarbonyl-6-fluoro-1-[3-hydroxy-3,3-bis(dimethoxyphosphono)-1-propyl]-7-(4-methyl-1-piperazyl)-4-oxo-1,4-dihydroquinoline. Hydrolysis of carboxylate and phosphonate ester groups of this compound yields the title compound.

In an alternative synthesis of the title compound, ethyl 2-(2,4-dichloro-5-fluoro-benzoyl)-3-ethoxyacrylate is reacted with (tetramethyl 3-amino-1-hydroxy-1,1-propanediphosphonate) in a solvent, as described in U.S. Pat. No. 4,292,007 for the analogous case of cyclopropylamine. Cyclization of the resulting substituted α-benzoyl-β-alkylamino acrylate as described in the same patent gives ethyl 7-chloro-6-fluoro-1-[3-hydroxy-3,3-bis(dimethoxyphosphono)-1-propyl]-4-oxo-1,4-dihydroquinoline-3-carboxylate. The latter is reacted with 1-methylpiperazine as described for the analogous reaction in Example 11 to give the ethyl ester at the carboxylate group and tetramethyl ester at the phosphonate groups of the title compound.

EXAMPLE 13

1-Cyclopropyl-7-{4-[3-hydroxy-3,3-bis(dimethoxyphosphono)-1-propyl]-1-piperazyl}-4-oxo-1,4-dihydro-1,6-naphthyridine-3-carboxylic acid 7-Chloro-1-cyclopropyl-4-oxo-1,4-dihydro-1,6-naphthyridine-3-carboxylic acid is prepared following the procedure of example 20(e) of U.S. Pat. No. 4,670,444. The acid then is employed in the procedure of example 1 of the cited patent except substituting for N-methylpiperazine an equivalent amount of 3-(1-piperazyl)-1-hydroxy-1,1-propanediphosphonic acid, tetramethyl ester, to yield 1-cyclopropyl-7-{4-[3-hydroxy-3,3-bis(dimethoxyphosphono)-1-propyl]-1-piperazyl}-4-oxo-1,4-dihydro-1,6-naphthyridine-3-carboxylic acid.

A tablet formulation is prepared from the following formulation:

| | |
|---|---|
| 1-cyclopropyl-7-{4-[3-hydroxy-3,3-bis(dimethoxyphosphono)-1-propyl]-1-piperazyl}-4-oxo-1,4-dihydro-1,6-naphthyridine-3-carboxylic acid | 290.0 mg |
| Avicel | 47.0 mg |
| Moist corn starch | 13.5 mg |
| Pregelatinized starch | 6.0 mg |
| Magnesium stearate | 3.5 mg |
| Film coating | |
| HPM cellulose | 3.0 mg |
| Polyethylene glycol 4000 | 1.0 mg |
| Titanium dioxide | 1.0 mg |

EXAMPLE 14

7-(4-Methylpiperazino)-1-cyclopropyl-4-oxo-1,4-dihydro-1,6-naphthyridine-3-{N-[5-hydroxy-5,5-bis(dimethoxyphosphono)pentyl]-carboxamide}

7-(4-Methylpiperazino)-1-cyclopropyl-4-oxo-1,4-dihydro-1,6-naphthyridine-3-carboxylic acid, which is prepared as described in U.S. Pat. No. 4,670,444, is converted to its acid chloride and reacted with $H_2N-(CH_2)_4-Z$ (tetramethyl 5-amino-1-hydroxy-1,1-pentanediphosphonate) and an excess of triethylamine to give, after product purification, 7-(4-methylpiperazino)-1-cyclopropyl-4-oxo-1,4-dihydro-1,6-naphthyridine-3-{N-[5-hydroxy-5,5-bis(dimethoxyphosphono)pentyl]-carboxamide}.

EXAMPLE 15

1-Cyclopropyl-6-fluoro-7-{4-[3-hydroxy-3,3-bis(dimethoxy-phosphono)-1-propyl]-1-piperazyl}-1,4-dihydro-4-oxo-quinoline-3-carboxylic acid 7-Chloro-1-cyclopropyl-6-fluoro-1,4-dihydro-4-oxo-quinoline-3-carboxylic acid is prepared according to the procedure of columns 7–8 of U.S. Pat. No. 4,670,444. The acid is then employed in the procedure of example 23 of the cited patent except substituting for piperazine an equivalent amount of 3-(1-piperazyl)-1-hydroxy-1,1-propanediphosphonic acid, tetramethyl ester to yield 1-cyclopropyl-6-fluoro-7-{4-[3-hydroxy-3,3-bis(dimethoxyphosphono)-1-propyl]-1-piperazyl}-1,4-dihydro-4-oxo-quinoline-3-carboxylic acid.

EXAMPLE 16

6-{2-Ethoxy-5-[3-hydroxy-3,3-bis(dimethoxyphosphono)-1-propylamino]naphthoyl}]-amino-3,3-dimethyl-7-oxo-4-thia-1-azabicyclo[3.2.0]heptane-2-carboxylic acid and isomers A mixture of 5-amino-2-ethoxy-1-naphthoic acid and 3-chloro-1-hydroxy-1,1-propanediphosphonic acid, tetramethyl ester) are heated in an alcohol solution containing 2 equivalents of base. Isolation and purification yield 2-ethoxy-5-[3-hydroxy-3,3-bis(dimethoxyphosphono)-1-propyl]-amino-1-naphthoic acid. The latter is condensed by the procedure disclosed in U.S. Pat. No. 3,132,136 with aminopenicillanate to afford 6-{2-ethoxy-5-[3-hydroxy-3,3-bis(dimethoxyphosphono)-1-propylamino]naphthoyl}-amino-3,3-dimethyl-7-oxo-4-thia-1-azabicyclo[3.2.0]heptane-2-carboxylic acid.

Substituting 3-amino-2-ethoxy-1-naphthoic acid for 5-amino-2-ethoxy-1-naphthoic acid in the foregoing procedure yields 6-{2-ethoxy-3-[3-hydroxy-3,3-bis(dimethoxyphosphono)-1-propylamino-naphthoyl}-amino-3,3-dimethyl-7-oxo-4-thia-1-azabicyclo[3.2.0]heptane-2-carboxylic acid.

Substituting 4-amino-2-ethoxy-1-naphthoic acid for 5-amino-2-ethoxy-1-naphthoic acid in the foregoing procedure yields 6-{2-ethoxy-4-[3-hydroxy-3,3-bis(dimethoxyphosphono)-1-propylamino]-naphthoyl}]-amino-3,3-dimethyl-7-oxo-4-thia-1-azabicyclo[3.2.0]heptane-2-carboxylic acid.

Substituting 6-amino-2-ethoxy-1-naphthoic acid for 5-amino-2-ethoxy-1-naphthoic acid in the foregoing procedure yields 6-{2-ethoxy-6-[3-hydroxy-3,3-bis(dimethoxyphosphono)-1-propylamino]-naphthoyl}-amino-3,3-dimethyl-7-oxo-4-thia-1-azabicyclo[3.2.0]heptane-2-carboxylic acid.

Substituting 7-amino-2-ethoxy-1-naphthoic acid for 5-amino-2-ethoxy-1-naphthoic acid in the foregoing procedure yields 6-{2-ethoxy-7-[3-hydroxy-3,3-bis(dimethoxyphosphono)-1-propylamino]-naphthoyl}-amino-3,3-dimethyl-7-oxo-4-thia-1-azabicyclo[3.2.0]heptane-2-carboxylic acid.

EXAMPLE 17

7β-[α-(Z-Methoxyimino)-α(2-aminothiazol-4-yl)acetamido]-3-(1-methyl-1,2,3-triazol-5-ylthiomethyl)-3-cephem-4-{N-[5-hydroxy-5,5-bis(dimethoxyphosphono)-1-pentyl]-carboxyamide}

7β-[α-(Z-Methoxyimino)-α(2-tert-butoxycarbonylaminothiazol-4-yl)-acetamido]-3-[(1-methyl-1,2,3-triazol-5-yl)thiomethyl]-3-cephem-4-carboxylic acid is treated with thionyl chloride in anhydrous methylene chloride, with cooling. After evaporation of the excess of thionyl chloride, the residue is treated with tetramethyl 5-amino-1-hydroxy-1,1-pentanediphosphonate and base. Removal of the tert-butoxycarbonyl protecting group with cold trifluoroacetic acid and anisole, isolation of product, and purification yield 7β-[α-(Z-methoxyimino)-α-(2-aminothiazol-4-yl)-acetamido]-3-[(1-methyl-1,2,3-triazol-5-yl)-thiomethyl]-3-cephem-4-{N-[5-hydroxy-5,5-bis(dimethoxyphosphono)-1-pentyl])-carboxamide}.

EXAMPLE 18

7β-[α-(Z-Methoxyimino)-α-(2-aminothiazol-4-yl)-acetamido]-3-{[4-hydroxy-4,4-bis(dimethoxyphosphono-1-butylcarbamoyl]-oxymethyl}-3-cephem-4-carboxylic acid 7β-[α-(Z-Methoxyimino)-α-(2-tert-butoxycarbonylaminothiazol-4-yl)-acetamido]-3-hydroxymethyl-3-cephem-4-carboxylic acid-tert-butyl ester is reacted with phosgene (toluene solution) in the presence of pyridine. The resulting chlorocarbonate is reacted without purification with tetramethyl 4-amino-1-hydroxy-1,1-butanediphosphonate in the presence of one equivalent of base, to give 7β-[α-(Z-methoxyimino)-α-(2-tert-butoxycarbonylaminothiazol-4-yl)-acetamido]-3-{[4-hydroxy-4,4-bis(dimethoxyphosphono)-1-butylcarbamoyl]-oxymethyl}-3-cephem-4-carboxylic acid-tert-butyl ester. Deprotection with trifluoroacetic acid and anisole gives 7β-[α-(Z-methoxyimino)-α-(2-aminothiazol-4-yl)-acetamido]-3-{[(4-hydroxy-4,4-bis(dimethoxyphosphone)-1-butylcarbamoyl]-oxymethyl}-3-cephem-4-carboxylic acid.

EXAMPLE 19

7β-[α-(Z-Methoxyimino)-α-(2-aminothiazol-4-yl)-acetamido]-3-{[4-hydroxy-4,4-bis(diethoxyphosphono)-butanoyloxy]-methyl}-3-cephem-4-carboxylic acid Tetraethyl 1-hydroxy-4-pentene-1,1-diphosphonate, prepared from 4-pentenoyl chloride as described for the analogous compound in Example __ is subjected to an ozonlysis-oxidationprotocol to give the 4-hydroxy-4,4-bis(diethoxyphosphone)-butanoic acid. The hydroxyl group of the latter is protected as tert-butoxycarbonate ester, after which the 4-(tert-butoxycarbonyloxy)-4,4-bis(diethoxyphosphono)-butanoyl chloride is prepared by reaction with oxaloyl chloride. The reaction of benzhydryl 7β-{α-(Z-methoxyimino)-α-[2-tert-butoxycarbonylamino)-thiazol-4-yl]-acetamido}-3-hydroxymethyl-3-cephem-4-carboxylate with the 4-(tert-butoxycarbonyloxy)-4,4-bis(diethoxyphosphono)-butanoyl chloride in the presence of pyridine leads to the benzhydryl ester of the 7β-{α-(Z-methoxyimino)-α-[2-tert-butoxycarbonyl-amino)-thiazyl-4-yl]-acetamido}-3-thiazol-4-yl]-acetamido}-3-{[4-(tert-butoxycarbonyloxy)-4,4-bis(diethoxyphosphono)-butanoyloxy]methyl}-3-cephem-4-carboxylic acid. Deprotection by reaction with cold trifluoroacetic acid and anisole yields 7β-[α-(Z-methoxyimino)-α-(2-aminothiazol-4-yl)-acetamido]-3-{[(4-hydroxy-4,4-bis(diethoxyphosphono)-butanoyloxy]-methyl}-3-cephem-4-carboxylic acid.

EXAMPLE 20

7β-{α-(Z-Methoxyimino)-α-[2-(3-hydroxy-3,3-bis(dimethoxyphosphono)-1-propylamino-thiazol-4-yl]-acetamido}-3-acetoxymethyl-3-cephem-4-carboxylic acid Reaction of Cl—(CH₂)₂—Z (3-chloro-1-hydroxy-1,1-propanediphosphonic acid, tetramethyl ester) with 7β-[α-(Z-methoxyimino)-α (2-aminothiazol-4-yl)-acetamido]-3-acetoxymethyl-3-cephem-4-carboxylic acid in the presence of sodium carbonate yields 7β-{α-(Z-methoxyimino)-α-[2-(3-hydroxy-3,3-bis(dimethoxyphosphono)-1-propylaminothiazolyl-4-yl]-acetamido}-3-acetoxymethyl-3-cephem-4-carboxylic acid.

EXAMPLE 21

7β-{α-(Z-Methoxyimino)-α-[2-(6-hydroxy-6,6-bis(diethoxyphosphono)-hexanoylamino)-thiazol-4-yl]-acetamidol-3-acetoxymethyl-3-cephem-4-carboxylic acid 6-Hydroxy-6,6-diphosphonohexanoic acid, tetramethyl ester is treated with tert-butoxycarbonyl chloride, and the 6-tert-butoxycarbonyloxy)-6,6-diphosphonohexanoic acid, tetramethyl ester thus formed is converted to the corresponding acid chloride with oxalyl chloride and pyridine. The acid chloride is condensed with 7β-[α-(Z-methoxyimino)-α-(2-aminothiazol-4-yl)-acetamido]-3-acetoxymethyl-3-cephem-4-carboxylic acid and, again in the presence of pyridine, and forms 7β-{α-(Z-methoxyimino)-α[2-(6-tert-butoxycarbonyloxy)-6,6-bis(diethoxyphosphono)hexanoyl-amino)-thiazol-4-yl]-acetamido}-3-acetoxymethyl-3-cephem-4-carboxylic acid. Deprotection with trifluoroacetic acid and anisole yields the title compound.

EXAMPLE 22

7β-{α-(Z-Methoxyimino)-α-[2-(3-hydroxy-3,3-bis(diethoxyphosphono)-propanoylamino)-thiazol-4-yl]-acetamido}-3-acetoxymethyl-3-cephem-4-carboxylic acid 3-Hydroxy-3,3-diphosphonopropanoic acid, tetramethyl ester is converted to 3-(tert-butoxycarbonyloxy)-3,3-bis(diethoxyphosphono)propionic acid and then to 3-(tert-butoxycarbonyloxy)-3,3-bis(diethoxyphosphono)propanoyl chloride. The acid chloride is then added to α-(Z-methoxyimino)-α-(2-aminothiazol-4-yl)-acetic acid and pyridine to form α-(Z-methoxyimino)-α-{2-[3-(tert-butoxycarbonyloxy)-3,3-bis(diethoxyphosphono)-propanoyl-amino]-thiazol-4-yl}-acetic acid. The latter is reacted with oxaloyl chloride to form the acid chloride, α-(Z-methoxyimino)-α-{2-[3-(tert-butoxycarbonyloxy)-3,3-bis(diethoxyphosphono)-propanoyl-amino)-thiazol-4-yl]-acetyl chloride. This acid chloride is reacted with 7β-amino-3-acetoxymethyl-3-cephem-4-carboxylic acid and pyridine and gives 7β-{α-(Z-methoxyimino)-α-[2-(3-tert-butoxycarbonyloxy)-3,3-bis(diethoxyphosphono)propanoyl-amino)-thiazol-4-yl]-acetamido}-3-acetoxymethyl-3-cephem-4-carboxylic acid. Deprotection with trifluoroacetic acid and anisole yields the title compound.

EXAMPLE 23

6R,7R-7[α-(Z-Methoxyimino)-α-(2-amino-thiazol-4-yl-acetamido]-3-{[2,5-dihydro-6-(4-hydroxy-4,4-bis(dimethoxy-phosphono)-1-butylaminocarbonyloxy)-2-methyl-5-oxo-as-triazin-3-yl]thio-methyl}-3-cephem-4-carboxylic acid 6R,7R-7{α-(Z-Methoxyimino)-α-[2-(tert-butoxycarbonylamino)-thiazol-4-yl]acetamido}-3-[(2,5-dihydro-6-hydroxy-2-methyl-5-oxo-as-triazin-3-yl)thio-methyl]-3-cephem-4-carboxylic acid benzhydryl ester is reacted as described in Example 18, first with phosgene and then with tetramethyl 4-amino-1-hydroxy-1,1-butanediphosphonoate, to form (6R,7R)-7{α-(Z-methoxyimino)-α-[2-(tert-butoxycarbonylamino)-thiazol-4-yl]acetamido}-3-[(2,5-dihydro-6-(4-hydroxy-4,4-bis(dimethoxyphosphono)-1-butylaminocarbonyloxy)-2-methyl-5-oxo-as-triazin-3-yl]thio-methyl}-3-cephem-4-carboxylic acid benzhhydryl ester. Deprotection with trifluoroacetic acid and anisole yields the title compound.

EXAMPLE 24

(6R,7R)-7-{α-(Z-Methoxyimino)-α-[2-(2-hydroxy-2,2-bis(dimethoxyphosphono)-1-ethylamino)-thiazol-4-yl]-acetamido}-3-[2,5-dihydro-6-hydroxy-2-methyl-5-oxo-as-triazin-3-yl)-thio-methyl]-3-cephem-4-carboxylic acid Reaction of Cl—CH$_2$—Z (2-chloro-1-hydroxy-1,1-ethanediphosphonic acid, tetramethyl ester) as described in Example 20 with 6R,7R)-7-[α-(Z-methoxyimino)-α-(aminothiazol-4-yl)-acetamido]-3-[2,5-dihydro-6-hydroxy-2-methyl-5-oxo-as-triazin-3-yl)-thio-methyl]-3-cephem-4-carboxylic acid gives the title compound.

EXAMPLE 25

7β-[5-Hydroxy-5,5-bis(dimethoxyphosphono)-1-pentylaminocarbonylamino]-7-methoxy-3-carbamoyloxymethyl-3-cephem-4-carboxylic acid 7β-Amino-7-methoxy-3-carbamoyloxymethyl-3-cephem-4-carboxylic acid is reacted with an excess of phosgene (in toluene solution) in the presence of pyridine. The 7-chlorocarbamoyl derivative thus formed is reacted with tetramethyl 5-amino-1-hydroxy-1,1-pentanediphosphonate and one equivalent of base, to yield the title compound.

EXAMPLE 26

7-[6-Hydroxy-6,6-bis(dimethoxyphosphono)-hexanoylamino]-7-methoxy-3-carbamoyloxymethyl-3-cephem-4-carboxylic acid 6-(tert-butoxycarbonyl)-6,6-diphosphonohexanoyl chloride, prepared as in Example 21, is reacted with 7β-amino-7-methoxy-3-carbamoyloxymethyl-3-cephem-4-carboxylic acid in the presence of pyridine. Deprotection with trifluoroacetic acid and anisole yields the title compound.

EXAMPLE 27

7β-(2-Thienylacetamido)-7-methoxy-3-{[3-hydroxy-3,3-bis(dimethoxyphosphono)-1-propylcarbamoyl]-oxymethyl}-3-cephem-4-carboxylic acid The benzhydryl ester of 7β-(2-thienylacetamido)-7-methoxy-3-hydroxymethyl-3-cephem-4-carboxylic acid is reacted first with phosgene and then with tetramethyl 3-amino-1-hydroxy-1,1-propane diphosphonate, by the procedure described in Example 18. Cleavage of the ester with trifluoroacetic acid yields 7β-(2-thienylacetamido)-7-methoxy-3-{[3-hydroxy-3,3-bis(dimethoxyphosphono)-1-propylcarbamoyl]-oxymethyl}-3-cephem-4-carboxylic acid.

EXAMPLE 28

7β-{5-[3-Hydroxy-3,3-bis(dimethoxyphosphono)-1-propylamino]-2-thienylacetamido}-7-methoxy-3-carbamoyloxymethyl-3-cephem-4-carboxylic acid 5-(2,2,2-trichloroethoxycarbonylamino)-2-thienylacetic acid is reacted with the benzhydryl ester of 7β-amino-7-methoxy-3-carbamoyloxymethyl-3-cephem-4-carboxylic acid in the presence of dicyclohexyl-carbodiimide. The reaction product, benzhydryl 7β-[5-(2,2,2-trichloroethoxycarbonylamino)-2-thienylacetamido]-7-methoxy-3-carbamoyloxymethyl-3-cephem-4-carboxylate, is treated with zinc dust in 90% formic acid and forms benzhydryl 7β-[5-amino-2-thienylacetamido]-7-methoxy-3-carbamoyloxymethyl-3-cephem-4-carboxylate. Reaction with 2-chloro-1-hydroxy-1,1-ethanediphosphonic acid tetramethyl ester as described in Example 24, followed by cleavage of the benzhydryl ester as described in Example 27, yields 7β-{5-[3-hydroxy-3,3-bis(dimethoxyphosphono)-1-propylamino]-2-thienylacetamido}-7-methoxy-3-carbamoyloxymethyl-3-cephem-4-carboxylic acid.

EXAMPLE 29

7β-{[5-(3-Hydroxy-3,3-bis(dimethoxyphosphono)-1-propylaminocarbonyl-amino)-2-thienyl]-acetamido}-7-methoxy-3-carbamoyloxymethyl-3-cephem-4-carboxylic acid The benzhydryl ester of 7β-[5-amino-2-thienylacetamido]-7-methoxy-3-carbamoyloxymethyl-3-cephem-4-carboxylic acid is reacted with phosgene and pyridine. The benzhydryl 73-[5-(chlorocarbonyl-amino)-2-thienylacetamido]-7-methoxy-3-carbamoyloxymethyl-3-cephem-4-carboxylate thus formed is treated with tetramethyl 3-amino-1-hydroxy-1,1-propanediphosphonate, as described in Example 25, and gives benzhydryl 7β-{[5-(3-hydroxy-3,3-bis(dimethoxyphosphono)-1-propylaminocarbonyl-amino)-2-thienyl]-acetamido}-7-methoxy-3-carbonyloxymethyl-3-cephem-4-carboxylate. Ester cleavage with trifluoroacetic acid yields the title compound.

EXAMPLE 30

7-Azido-7-{[(5-hydroxy-5,5-bis(dimethoxyphosphono)-1-pentylamino]-carbonyl}-3-carbamoyloxymethyl-3-cephem-4-carboxylic acid The benzhydryl ester of 7-azido-7-chlorocarbonyl-3-acetoxymethyl-3-cephem-4-carboxylic acid, prepared as described in example 109 of U.S. Pat. No. 4,338,437, is reacted with tetramethyl 5-amino-1-hydroxy-1,1-pentanediphosphonate and sodium carbonate to give benzhydryl 7-azido-7-{[5-hydroxy-5,5-bis(dimethoxyphosphono)-1-pentylamino]-carbonyl}-3-acetoxymethyl-3-cephem-4-carboxylate. Selective hydrolysis of the acetate ester with citrus acetyl enzyme, as described by Jeffery et al., *Biochem. J.* 1961, 81, 591, produces benzhydryl 7-azido-7-{[(5-hydroxy-5,5-bis(dimethoxyphosphono)-1-pentylamino]-carbonyl}-3-hydroxymethyl-3-cephem-4-carboxylate. The latter is reacted with carbamoyl chloride in the presence of pyridine and gives benzhydryl 7-azido-7-{[5-hydroxy-5,5-bis(dimethoxyphosphono)-1-pentylamino]-carbonyl}-3-carbamoyloxymethyl-3-cephem-4-carboxylate. Cleavage of the benzhydryl ester group with trifluoroacetic acid gives 7-azido-7-{[5-hydroxy-5,5-bis(dimethoxyphosphono)-1-pentylamino]-carbonyl}-3-carbamoyloxymethyl-3-cephem-4-carboxylic acid.

EXAMPLE 31

7-Azido-7-{[5-hydroxy-5,5-bis(dimethoxyphosphono)-1-pentylamino]-carbonyl}-3-acetoxymethyl-3-cephem-4-carboxylic acid Cleavage of benzhydryl 7-azido-7-{[5-hydroxy-5,5-bis(dimethoxyphosphono)-1-pentylamino]-carbonyl}-3- acetoxymethyl-3-cephem-4-carboxylate, prepared as described in Example 30, with trifluoroacetic acid gives 7-azido-7-{[5-hydroxy-5,5-bis(dimethoxyphosphono)-1-pentylamino]-carbonyl}-3-acetoxymethyl-3-cephem-4-carboxylic acid.

EXAMPLE 32

7-(2-Thienylacetamido)-7-{5-hydroxy-5,5-bis(dimethoxyphosphono)-1-pentylamino]-carbonyl}-3-carbamoyloxymethyl-3-cephem-4-carboxylic acid The 7-azido-7-{[5-hydroxy-5,5-bis(dimethoxyphosphono)-1-pentylamino]-carbonyl}-3-carbamoyloxymethyl-3-cephem-4-carboxylic acid, obtained as described in Example 30, is hydrogenated at atmospheric pressure with hydrogen in the presence of platinum oxide as catalyst and gives 7-amino-7-{[5-hydroxy-5,5-bis(dimethoxyphosphono)-1-pentylamino]-carbonyl}-3-carbamoyloxymethyl-3-cephem-4-carboxylic acid. Reaction of the latter with 2-thienylacetyl chloride and pyridine yields 7-(2-thienyl-acetamido)-7-{[5-hydroxy-5,5-bis(dimethoxyphosphono)-1-pentylamino]-carbonyl}-3-carbamoyloxymethyl-3-cephem-4-carboxylic acid.

EXAMPLE 33

4-Methoxy-6,7,9,11-tetrahydroxy-9-{[5-hydroxy-5,5-bis(dimethoxyphosphono)-1-pentylamino]-acetyl}-5,7,8,9,10,12-hexahydro-tetracene-5,12-dione 4-Methoxy-6,7,9,11-tetrahydroxy-9-bromoacetyl-5,7,8,9,10,12-hexahydro-tetracene-5,12-dione is prepared as described in U.S. Pat. No. 3,803,124 and it is reacted with tetramethyl 5-amino-1-hydroxy-1,1-pentanediphosphonate and potassium carbonate to yield 4-methoxy-6,7,9,11-tetrahydroxy-9-{[5-hydroxy-5,5-bis(dimethoxyphosphono-1-pentylamino]-acetyl}-5,7,8,9,10,12-hexahydro-tetracene-5,12-dione.

EXAMPLE 34

4-Methoxy-6,7,9,11-tetrahydroxy-9-{[3-hydroxy-3,3-bis(dimethoxyphosphono)-1-propylaminocarbonyloxy]-acetyl}-5, 78,9,10,12-hexahydrotetracene-5,12-dione 4-Methoxy-6,7,9,11-tetrahydroxy-9-acetyl-5,7,8,9,10,12-hexahydro-tetracene-5,12-dione is prepared as described in U.S. Pat. No. 3,803,124 and the hydroxyl groups are protected as (2-methoxyethoxy)-methyl ethers by reaction with (2-methoxyethoxy)-methyl chloride, $CH_3-O-CH_2-CH_2-O-CH_2Cl$. The 4-methoxy-6,7,9,11-tetra-[(2-methoxyethoxy)-methoxy]-9-acetyl-5,7,8,9,10,12-hexahydro-tetracene-5,12-dione thus formed is converted to the 9-bromoacetyl derivative by reaction with bromine in methanol solution, and to the 9-hydroxyacetyl derivative by reaction with sodium hydroxide, as described for the non-etherified compounds in U.S. Pat. No. 3,803,124. Reaction with phosgene and then with tetramethyl 3-amino-1-hydroxy-1,1-propanediphosphonate affords 4-methoxy-6,7,9,11-tetra-[(2-methoxyethoxy)-methoxy]-9-{[3-hydroxy-3,3-bis(dimethoxyphosphono)-1-propylaminocarbonyloxy]-acetyl}-5,7,8,9,10,12-hexahydro-tetracene-5,12-dione. Deprotection is accomplished by reaction with fluoroboric acid, as described by Ikota et al., *J. Soc. Chem. Commun.* 1978, 869, and yields 4-methoxy-6,7,9,11-tetrahydroxy-9-{[3-hydroxy-3,3-bis(dimethoxyphosphono)-1-propylaminocarbonyloxy]-acetyl}-5,7,8,9,10,12-hexahydro-tetracene-5,12-dione.

EXAMPLE 35

4-Methoxy-6,7,9,11-tetrahydroxy-9-{[1-hydroxy-1,1-bis(dimethoxyphosphono)-2-propylaminocarbonyloxy]-acetyl}-5,7,8,9,10,12-hexahydro-tetracene-5,12-dione The 4-methoxy-6,7,9,11-tetra-[(2-methoxyethoxy)-methoxy]-9-bromoacetyl-5,7,8,9,10,12-hexahydro-tetracene-5,12-dione compound whose preparation is described in Example 34 is treated with 2-amino-1-hydroxy-1,1-propanediphosphonic acid tetramethyl ester as described for the analogous compound in Example 33. Removal of the protecting groups as described in Example 30 yields 4-methoxy-6,7,9,11-tetrahydroxy-9-{[1-hydroxy-1,1-bis(dimethoxyphosphono)-2-propylamino-carbonyloxy]-acetyl}-5,7,8,9,10,12-hexahydro-tetracene-5,12-dione.

EXAMPLE 36

1,6-Bis-{$N_1$:$N_1$-[4-chloro-3-(hydroxy-bis(dimethoxyphosphono-methyl)-phenyl]-diguanido-$N_{5_1}$:;$N_5'$}-hexane 2-Chloro-5-aminobenzoic acid is reacted with phosphorous acid and phosphorus trichloride according to Equation I to form α-hydroxy-(2-chloro-5-aminophenyl)-methanediphosphonic acid, which is converted to its tetramethyl ester as described in Example 1, and then is reacted by the procedure described for an analogous compound in U.S. Pat. No. 2,684,924 with hexamethylene-bis-dicyanamide and yields 1,6-bis-{$N_1$:$N_1$'-[4-chloro-3-(hydroxy-bis(dimethoxyphosphono-methyl)-phenyl]-diguanido-$N_5$:$N_5'$}-hexane.

What is claimed is:

1. A method for preparing a compound of the formula A—$(V)_m$—$(R)_n$—Z, wherein A is the residue of a pharmaceutically active antibiotic chemical entity, V is O, S, NR', CONR', CO—O, O—CO, O—CO—O, CO—S, S—CO, S—CO—S, NR'—CO, OCO—NR', NR'—CO—O, NR'—CO—NR", CO—NR", CO—NR'—NR", NR'—NR"—CO, NR'—C(=NH)—NR" or NR'—C(=NH)—NH—C(=NH)—NR" wherein R, R' and R" are H or an organic or heteroorganic group, and m and n are each 1, or one of m and n is 0, comprising reacting a pharmaceutically active antibiotic entity of the formula A—V' wherein V' is halogen, OH, SH, NR'R", COOR', CO—X wherein X is halogen or azido, O—CO—X wherein X is halogen, O—CO—OR', CO—SR', S—CO—X, NR'—CO—X, NR'—NHR", NR'—CN, NR'—C(=NH)—NH—CN, or metal (covalently bound or ionic), with a diphosphonate compound of the formula V'—R—Z wherein V' and R have the previous meanings and Z is

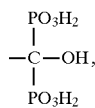

which optionally may be protected, the composition of V' in the pharmaceutically active chemical entity of formula A—V' and in the diphosphonate compound of formula V'—R—Z being different and being selected to permit a condensation reaction therebetween.

2. A method for preparing a compound of claim 1 of the formula A—Z, comprising subjecting a compound of formula A—V', wherein A and Z have the same meaning as in claim 1, and V' is COOH, to conditions effective to convert the COOH group to Z.

3. A method according to claim 1 wherein V is NH, said compound being formed from a pharmaceutically active chemical entity wherein V' is halogen, amino, or a sulfonate ester, and a diphosphonate compound wherein V' is amino or halogen.

4. A method according to claim 1 wherein V is a tertiary amino-containing group, said compound being formed from a pharmaceutically active chemical entity wherein V' is halogen, a sulfonate ester or a secondary amino-containing group, and a diphosphonate compound wherein V' is a secondary amino-containing group or halogen.

5. A method according to claim 1 wherein V is CONR', said compound being formed from a pharmaceutically active chemical entity wherein V' is carboxyl, and a diphosphonate compound wherein V' is primary or secondary amino.

6. A method according to claim 1 wherein V is NR'CO, said compound being formed from a pharmaceutically active chemical entity wherein V' is primary or secondary amino, and a diphosphonate compound wherein V' is carboxyl.

7. A method according to claim 1 wherein V is CO—O, said compound being formed from a pharmaceutically active chemical entity wherein V' is carboxyl or a reactive carboxyl group derivative, and a diphosphonate compound wherein V' is halogen or hydroxyl.

8. A method according to claim 1 wherein V is O—CO, said compound being formed from a pharmaceutically active chemical entity wherein V' is halogen or hydroxyl, and a diphosphonate compound wherein V' is carboxyl.

9. A compound of the formula A—(V)$_m$—(R)$_n$—Z, wherein A, V, R, and Z have the same meaning as in claim 1, and m and n are independently 0 or 1.

10. An intermediate for a compound of claim 9 having the name
1-(3-hydroxy-3,3-diphosphonopropyl)-piperazine,
4-(1-piperazyl)-1-hydroxy-1,1-butanediphosphonic acid,
1-(2-hydroxy-2,2-diphosphonoethyl)-piperazine,
2-(1-piperazyl)-1-hydroxy-1,1-ethanediphosphonic acid,
(2,3-difluoro-6-nitrophenoxy)-pyruvic acid,
7,8-difluoro-[1,4]benzoxazine-3-carboxylic acid,
7,8-difluoro-3-(hydroxy-diphosphonomethyl)-[1,4]benzoxazine,
9,10-difluoro-3-hydroxydiphosphonomethyl)-7-oxo-2,3-dihydro-7H-pyrido[1,2,3-de][1,4]benzoxazine-6-carboxylic acid,
7-chloro-3-ethoxycarbonyl-6-fluoro-1-(3-hydroxy-3,3-diphosphono-1-propyl)-4-oxo-1,4-dihydroquinoline,
3-ethoxycarbonyl-6-fluoro-1-(3-hydroxy-3,3-diphosphono-1-propyl)-7-(4-methyl-1-piperazyl)-4-oxo-1,4-dihydroquinoline,
7-chloro-6-fluoro-1-(3-hydroxy-3,3-diphosphono-propyl)-4-oxo-1,4-dihydroquinoline-3-carboxylate,
2-ethoxy-5-(3-hydroxy-3,3-diphosphono-1-propyl)-amino-1-naphthoic acid,
7β-[α-(Z-methoxyimino)-α-(2-tert-butoxycarbonylaminothiazol-4-yl)-acetamido]-3-[(4-hydroxy-4,4-diphosphono-1-butylcarbamoyl)-oxymethyl]-3-cephem-4-carboxylic acid-tert-butyl ester,
3-cyano-1-hydroxypropane-1,1-diphosphonic acid,
3-(tert-butoxycarbonyloxy)-3,3-diphosphonopropionic acid,
4-(tert-butoxycarbonyloxy)-4,4-diphosphonobutanoic acid,
4-(tert-butoxycarbonyloxy)-4,4-diphosphono-butanoyl chloride,
7β-{α-(Z-methoxyimino)-α-[2-tert-butoxycarbonyl-amino)-thiazol-4-yl]-acetamido}-3-[4-(tert-butoxycarbonyloxy)-4,4-diphosphono-butanoyloxymethyl]-3-cephem-4-carboxylic acid,
7β-[5-(3-hydroxy-3,3-diphosphono-1-propylamino)-2-thienylacetamido]-7-methoxy-3-carbamoyloxymethyl]-3-cephem-4-carboxylic acid,
3-(tert-butoxycarbonyloxy)-3,3-diphosphonopropanoyl chloride,
α-(Z-methoxyimino)-α-[2-(3-(tert-butoxycarbonyloxy)-3,3-diphosphonopropanoyl-amino)-thiazol-4-yl]-acetic acid,
α-(Z-methoxyimino)-α-[2-(3-(tert-butoxycarbonyloxy)-3,3-diphosphonopropanoyl-aminothiazol-4-yl]-acetyl chloride,
7β-{α-(Z-methoxyimino)-α-[2-(3-tert-butoxycarbonyloxy)-3,3-diphosphonopropanoyl-amino)-thiazol-4-yl]-acetamido}-3-acetoxymethyl-3-cephem-4-carboxylic acid,
(6R,7R)-7{α-(Z-methoxyimino)-α-[2-(tert-butoxycarbonyl-amino)-thiazol]-4-yl]acetamido}-3-[(2,5-dihydro-6-(4-hydroxy-4,4-diphosphono-1-butylaminocarbonyloxo)-2-methyl-5-oxo-as-triazin-3-yl]thio-methyl}-3-cephem-4-carboxylic acid benzhhydryl ester,
benzhydryl 7β-{[5-(3-hydroxy-3,3-diphosphono-1-propylaminocarbonyl-amino)-2-thienyl]-acetamido}-7-methoxy-3-carbonyloxymethyl-3-cephem-4-carboxylate,
benzhydryl 7-azido-7-[(5-hydroxy-5,5-diphosphono-1-pentylamino)-carbonyl]-3-acetoxymethyl-3-cephem-4-carboxylate,
benzhydryl 7-azido-7-[(5-hydroxy-5,5-diphosphono-1-pentylamino)-carbonyl]-3-hydroxymethyl-3-cephem-4-carboxylate,
7-azido-7-[(5-hydroxy-5,5-diphosphono-1-pentylamino)-carbonyl]-3-carbamoyloxymethyl-3-cephem-4-carboxylic acid,
7-amino-7-[(5-hydroxy-5,5-diphosphono-1-pentylamino)-carbonyl]-3-carbamoyloxymethyl-3-cephem-4-carboxylic acid,
4-methoxy-6,7,9,11-tetra-[(2-methoxyethoxy)-methoxy]-9-[(3-hydroxy-3,3-diphosphono-1-propylaminocarbonyloxy)-acetyl]-5,7,8,9,10,12-hexahydro-tetracene-5,12-dione,
4-methoxy-6,7,9,11-tetrahydroxy-9-[(3-hydroxy-3,3-diphosphono-1-propylaminocarbonyloxy)-acetyl]-5,7,8,9,10,12-hexahydro-tetracene-5,12-dione, or
α-hydroxy-(2-chloro-5-aminophenyl)-methanediphosphonic acid.

11. A composition comprising a pharmaceutically effective amount of a compound of claim 9 and a pharmaceutically acceptable carrier.

12. A method of treating diseases selected from the group consisting of osteomyelitis, periodontal disease, urinary tract infections, infectious urinary tract stones, and bone cancer, comprising administering a compound of claim 9 in an amount effective to treat said disease.

13. A compound of claim 9 wherein A is the residue of a pharmaceutically active antibiotic compound selected fron the group consisting of an aminoglycoside, an amphenicol, an ansamycin, a β-lactam, a diaminopyrimidine, a lincosamide, a macrolide, a monobactam, a nitrofuran, an oxacephem, a polypeptide, a quinolone, a quinolone analog, a sulfonamide, a sulfone and a tetracycline.

14. A compound of claim 9 wherein V is O, S, NR', CONR', CO—O, O—CO, O—CO—O, CO—S, S—CO, S—CO—S, NR'—CO, OCO—NR', NR'—CO—O, NR'—CO—NR", CO—NR'—NR", NR'—NR"—CO, NR'—C(=NH)—NR" or NR'—C(=NH)—NH—C(=NH)—NR".

15. A compound according to claim 14 wherein V is NR', CONR', OCO—NR', NR'—CO—NR", CO—NR'—NR", NR—C(=NH)—NR" or NR'—C(=NH)—NH—C(=NH)—NR".

16. A compound according to claim 14 wherein V is CO—O, O—CO, O—CO—O, S—CO, NR'—CO, NR'—CO—O, or NR'—NR"—CO.

17. A compound according to claim 14 wherein V is O, S, CO—S or S—CO—S.

18. A compound of claim 9 having the name
9-fluoro-3-methyl-10-[4-(4-hydroxy-4,4-diphosphono-1-butyl)-1-piperazyl]-7-oxo-2,3-dihydro-7H-pyrido[1,2,3-de][1,4]benzoxazine-6-carboxylic acid,
9-fluoro-10-[4-(3-hydroxy-3,3-diphosphono-1-propyl)-1-piperazyl ]-7-oxo-2,3-dihydro-7H-pyrido-[1,2,3-de][1,4]benzoxazine-6-carboxylic acid,
9-chloro-3-methyl-10-[4-(2-hydroxy-2,2-diphosphono-ethyl)-1-piperazyl]-7-oxo-2,3-dihydro-7H-pyrido[1,2,3-de][1,4]-benzoxazine-6-carboxylic acid,
9-fluoro-3-methyl-10-[4-(2-hydroxy-2,2-diphosphono-1-ethyl)-1-piperazyl]-7-oxo-2,3-dihydro-7H-pyrido[1,2,3-de][1,4]-benzoxazine-6-carboxylic acid,
9-fluoro-3-methyl-10-(3-hydroxy-3,3-diphosphono-1-propylamino)-7-oxo-2,3-dihydro-7H-pyrido[1,2,3-de][1,4]benzoxazine-6-carboxylic acid,
9-fluoro-3-(hydroxy-diphosphonomethyl)-10-(4-methyl-1-piperazyl)-7-oxo-2,3-dihydro-7H-pyrido[1,2,3-de][1,4]benzoxazine-6-carboxylic acid,
9-fluoro-3-methyl-6-(hydroxydiphosphono-methyl)-10-(4-methyl-1-piperazyl)-7-oxo-2,3-dihydro-7H-pyrido[1,2,3-de][1,4]benzoxazine,
6-chloro-1-ethyl-7-[4-(3-hydroxy-3,3-diphosphonopropyl)-1-piperazyl]-4-oxo-1,4-dihydroquinoline-3-carboxylic acid,
6-fluoro-1-methyl-7-(4-hydroxy-4,4-diphosphono-1-butylamino)-4-oxo-1,4-dihydroquinoline-3-carboxylic acid,
6-chloro-1-ethyl-3-(hydroxy-diphosphonomethyl)-7-(4-methyl-1-piperazyl)-4-oxo-1,4-dihydro-quinoline,
6-chloro-7-(6-hydroxy-6,6-diphosphono-1-hexylamino)-1-methyl-4-oxo-1,4-dihydroquinoline-3-carboxylic acid,
6-fluoro-1-(3-hydroxy-3,3-diphosphono-1-propyl)-7-(-4-methyl-1-piperazyl)-4-oxo-1,4-dihydroquinoline-3-carboxylic acid,
1-cyclopropyl-7-[4-(3-hydroxy-3,3-diphosphono-1-propyl)-1-piperazyl]-4-oxo-1,4-dihydro-1,6-naphthyridine-3-carboxylic acid,
6-fluoro-7-(6-hydroxy-6,6-diphosphono-1-hexylamino)-1-methyl-4-oxo-1,4-dihydroquinoline-3-carboxylic acid,
7-(4-methylpiperazino)-1-cyclopropyl-4-oxo-1,4-dihydro-1,6-naphthyridine-3-[N-(5-hydroxy-5,5-diphosphonopentyl)-carboxamide,
1-cyclopropyl-6-fluoro-7-[4-(3-hydroxy-3,3-diphosphono-1-propyl)-1-piperazyl]-1,4-dihydro-4-oxo-quinoline-3-carboxylic acid,
6-[2-ethoxy-5-(3-hydroxy-3,3-diphosphono-1-propyl)-aminonaphthoyl]-amino-3,3-dimethyl-7-oxo-4-thia-1-azabicyclo[3.2.0]heptane-2-carboxylic acid,
6-[2-ethoxy-3-(3-hydroxy-3,3-diphosphono-1-propyl)-aminonaphthoyl]-amino-3,3-dimethyl-7-oxo-4-thia-1-azabicyclo[3.2.0]heptane-2-carboxylic acid,
6-[2-ethoxy-4-(3-hydroxy-3,3-diphosphono-1-propyl)-aminonaphthoyl]-amino-3,3-dimethyl-7-oxo-4-thia-1-azabicyclo[3.2.0]heptane-2-carboxylic acid,
6-[2-ethoxy-6-(3-hydroxy-3,3-diphosphono-1-propyl)-aminonaphthoyl]-amino-3,3-dimethyl-7-oxo-4-thia-1-azabicyclo[3.2.0]heptane-2-carboxylic acid,
6-[2-ethoxy-7-(3-hydroxy-3,3-diphosphono-1-propyl)-aminonaphthoyl]-amino-3,3-dimethyl-7-oxo-4-thia-1-azabicyclo[3.2.0]heptane-2-carboxylic acid,
7β-[α-(Z-methoxyimino)-α-(2-aminothiazol-4-yl)-acetamido]-3-[(1-methyl-1,2,3-triazol-5-yl)-thiomethyl]-3-cephem-4-[N-(5-hydroxy-5,5-diphosphonopentyl)-carboxamide],
7β-[α-(Z-methoxyimino)-α-(2-aminothiazol-4-yl)-acetamido]-3-[(4-hydroxy-4,4-diphosphono-1-butylcarbamoyl)-oxymethyl]-3-cephem-4-carboxylic acid,
7β-[α-(Z-methoxyimino)-α-(2-aminothiazol-4-yl)-acetamido]-3-[(4-hydroxy-4,4-diphosphonobutanoyloxy)-methyl]-3-cephem-4-carboxylic acid,
7β-[α-(Z-methoxyimino)-α-[2-(3-hydroxy-3,3-diphosphonopropylamino)-thiazol-4-yl]-acetamido}-3-acetoxymethyl-3-cephem-4-carboxylic acid,
7β-{α-(Z-Methoxyimino)-α-[2-(6-hydroxy-6,6-diphosphono-hexanoylamino)-thiazol-4-yl]-acetamido}-3-acetoxymethyl-3-cephem-4-carboxylic acid,
7β-{α-(Z-Methoxyimino)-α-[2-(3-hydroxy-3,3-diphosphono-propanoylamino)-thiazol-4-yl]-acetamido}-3-acetoxymethyl-3-cephem-4-carboxylic acid,
6R,7R-7[α-(Z-Methoxyimino)-α-(2-amino-thiazol-4-yl-acetamido]-3-{[2,5-dihydro-6-(4-hydroxy-4,4-diphosphono-1-butylaminocarbonyloxy)-2-methyl-5-oxo-as-triazin-3-yl]thio-methyl}-3-cephem-4-carboxylic acid,
(6R,7R)-7-{α-(Z-Methoxyimino)-α-[2-(2-hydroxy-2,2-diphosphono-1-ethylamino)-thiazol-4-yl]-acetamido}-3-[2,5-dihydro-6-hydroxy-2-methyl-5-oxo-as-triazin-3-yl)-thio-methyl]-3-cephem-4-carboxylic acid,
7β-(5-Hydroxy-5,5-diphosphono-1-pentylaminocarbonylamino)-7-methoxy-3-carbamoyloxymethyl-3-cephem-4-carboxylic acid,
7β-(6-Hydroxy-6,6-diphosphono-1-hexanoylamino)-7-methoxy-3-carbamoyloxymethyl-3-cephem-4-carboxylic acid,
7β-(2-thienylacetamido)-7-methoxy-3-[(3-hydroxy-3,3-diphosphono-1-propylcarbamoyl)-oxymethyl]-3-cephem-4-carboxylic acid,
7β-[5-(3-hydroxy-3,3-diphosphono-1-propylamino)-2-thienylacetamido]-7-methoxy-3-carbamoyloxymethyl]-3-cephem-4-carboxylic acid,
7β-{[5-(3-Hydroxy-3,3-diphosphono-1-propylaminocarbonyl-amino)-2-thienyl]-acetamido}-7-methoxy-3-carbamoyloxymethyl-3-cephem-4-carboxylic acid,
7-azido-7-[(5-hydroxy-5,5-diphosphono-1-pentylamino)-carbonyl]-3-carbamoyloxymethyl-3-cephem-4-carboxylic acid,
7-azido-7-[(5-hydroxy-5,5-diphosphono-1-pentylamino)-carbonyl]-3-acetoxymethyl-3-cephem-4-carboxylic acid,
7-(2-thienyl-acetamido)-7-[(5-hydroxy-5,5-diphosphone-1-pentylamino)-carbonyl]-3-carbamoyloxymethyl-3-cephem-4-carboxylic acid,
4-methoxy-6,7,9,11-tetrahydroxy-9-[(5-hydroxy-5,5-diphosphono-1-pentylamino)-acetyl]-5,7,8,9,10,12-hexahydro-tetracene-5,12-dione,
4-methoxy-6,7,9,11-tetrahydroxy-9-[(3-hydroxy-3,3-diphosphono-1-propylaminocarbonyloxy)-acetyl]-5,7,8,9,10,12-hexahydro-tetracene-5,12-dione,
4-methoxy-6,7,9,11-tetrahydroxy-9-[1-hydroxy-1,1-diphosphono-2-propylaminocarbonyloxy)-acetyl]-5,7,8,9,10,12-hexahydro-tetracene-5,12-dione, or 1,6-bis-{$N_1$:$N_1'$-[4-chloro-3-(hydroxy-diphosphono-methyl)-phenyl]-diguanido-$N_5$:$N_5'$} hexane,
and the pharmaceutically acceptable mono-, di-, tri and tetraesters thereof.

19. A compound of claim 13 wherein the β-lactam is selected from the group consisting of carbapenems, cephalosporins, cephamycins, and penicillins.

20. A compound of claim 9 wherein in any individual compound only one of the following conditions exist:
 (a) both m and n are 0,
 (b) both m and n are 1, or
 (c) one of m and n is 1 and the other is 0.

* * * * *